(12) United States Patent
O'Flaherty et al.

(10) Patent No.: US 10,828,349 B2
(45) Date of Patent: Nov. 10, 2020

(54) TREATMENT OF MICROBIAL INFECTIONS

(75) Inventors: Vincent O'Flaherty, Moycullen (IE); Paul McCay, Newcastle (IE)

(73) Assignee: NATIONAL UNIVERSITY OF IRELAND, GALWAY, Galway (IE)

( * ) Notice: Subject to any disclaimer, the term of this patent is extended or adjusted under 35 U.S.C. 154(b) by 439 days.

(21) Appl. No.: 14/111,236

(22) PCT Filed: Apr. 16, 2012

(86) PCT No.: PCT/EP2012/056946
§ 371 (c)(1),
(2), (4) Date: Jan. 21, 2014

(87) PCT Pub. No.: WO2012/140272
PCT Pub. Date: Oct. 18, 2018

(65) Prior Publication Data
US 2014/0134213 A1    May 15, 2014

(30) Foreign Application Priority Data

Apr. 15, 2011 (EP) .................................. 11162678

(51) Int. Cl.
| | | |
|---|---|---|
| *A61K 38/54* | (2006.01) | |
| *A61K 33/18* | (2006.01) | |
| *A61K 38/44* | (2006.01) | |
| *A61K 38/47* | (2006.01) | |
| *A61K 45/06* | (2006.01) | |
| *A61K 31/26* | (2006.01) | |
| *A61K 9/00* | (2006.01) | |
| *A61K 33/04* | (2006.01) | |
| *A61K 33/40* | (2006.01) | |

(52) U.S. Cl.
CPC ............ *A61K 38/54* (2013.01); *A61K 9/0041* (2013.01); *A61K 31/26* (2013.01); *A61K 33/04* (2013.01); *A61K 33/18* (2013.01); *A61K 33/40* (2013.01); *A61K 38/44* (2013.01); *A61K 38/443* (2013.01); *A61K 38/47* (2013.01); *A61K 45/06* (2013.01); *A61K 9/0073* (2013.01)

(58) Field of Classification Search
None
See application file for complete search history.

(56) References Cited

U.S. PATENT DOCUMENTS

| | | | | |
|---|---|---|---|---|
| 4,011,312 A * | 3/1977 | Reuter | ................. | A61K 9/0041 424/115 |
| 4,726,945 A | 2/1988 | Patel et al. | | |
| 4,726,948 A | 2/1988 | Prieels et al. | | |
| 5,575,993 A * | 11/1996 | Ward | ..................... | A01N 33/12 252/301.35 |
| 5,607,681 A | 3/1997 | Galley et al. | | |
| 6,312,687 B1 | 11/2001 | Guthrie et al. | | |
| 2006/0058273 A1* | 3/2006 | Cox | ..................... | A61K 9/0041 514/171 |
| 2007/0116698 A1* | 5/2007 | Perraudin | .............. | A61K 38/40 424/94.61 |
| 2008/0299103 A1* | 12/2008 | George | .................... | A61K 8/20 424/94.4 |
| 2011/0008361 A1 | 1/2011 | Bragger | | |
| 2012/0128650 A1* | 5/2012 | Bragger | ............... | A61K 9/0041 424/94.4 |

FOREIGN PATENT DOCUMENTS

| | | |
|---|---|---|
| WO | 20081004128 | 1/2008 |
| WO | 20101134827 | 11/2010 |
| WO | 20111074992 | 6/2011 |

OTHER PUBLICATIONS

"Benefits and Potential Risks of the Lactoperoxidase system of Raw Milk Preservation", Report of an FAO/WHO Technical Meeting FAO Headquarters, Rome, Italy, Nov. 28-Dec. 2, 2005, 73 pgs.
Curtin; et al., "Linezolid compared with eperezolid, vancomycin, and gentamicin in an in vitro model of antimicrobial lock therapy for Staphylococcus epidermidis central venous catheter-related biofilm infections", Antimicrob Agents Chemother (Oct. 2003), 47(10):3145-8.
Fricks-Lima; et al., "Differences in biofilm formation and antimicrobial resistance of Pseudomonas aeruginosa isolated from airways of mechanically ventilated patients and cystic fibrosis patients", Int J Antimicrob Agents (Apr. 2011), 37(4):309-15.
Garcia-Garibay; et al., Antimicrobial effect of the lactoperoxidase system in milk activated by immobilized enzymes, Food Biotechnology (1995), 9(3):157-166.
Ishido; et al., "Continuous supply of OSCN' ions by lactoperoxidase system developed from lactose as the primary substrate and its antibacterial activities", Milchwissenschaft (2011), 66(1).
Kussendrager; et al., "Lactoperoxidase: physico-chemical properties, occurrence, mechanism of action and applications", British Journal of Nutrition (Nov. 2000), 84(Suppl 1):S19-25.
Lambrechts; et al., "Photodynamic therapy for *Staphylococcus aureus* infected burn wounds in mice", Photochem Photobiol Sci (Jul. 2005), 4(7):503-9.

(Continued)

*Primary Examiner* — Celeste A Roney
(74) *Attorney, Agent, or Firm* — Leason Ellis LLP

(57) ABSTRACT

The present application relates to an anti-microbial system for use in the treatment of microbial infections or control of microbial contamination, which avoids the use of antibiotics. Such infections include mastitis, tuberculosis, cystic fibrosis and the contamination that may result from biofilm formation on medical devices.

20 Claims, 8 Drawing Sheets

(56) References Cited

OTHER PUBLICATIONS

Patent Cooperation Treaty (PCT) International Search Report dated Sep. 27, 2012, for PCT/EP2012/056946 (filed Apr. 16, 2012), 7 pgs.
Rainard; et al., "Innate immunity of the bovine mammary gland", Vet Res (May-Jun. 2006), 37(3):369-400.
Sakai; et al., "Generation of hydrogen peroxide by a low molecular weight compound in whey of Holstein dairy cows", Journal of Dairy Research (Aug. 2008), 75(3):257-61.
Sakai; et al., "Production of hydrogen peroxide by a small molecular mass compound in milk from Holstein cows with high and low milk somatic cell count", Journal of Dairy Research (Aug. 2008), 75(3):355-9.
Sandholm; et al., "Glucose oxidase (GOD) as a source of hydrogen peroxide for the lactoperoxidase (LPO) system in milk: antibacterial effect of the GOD-LPO system against mastitis pathogens", Zentralbl Veterinarmed B. (Jun. 1988), 35(5):346-52.
Seifu; et al. "Significance of the lactoperoxidase system in the dairy industry and its potential applications: a review", Trends in Food Science & Technology (Apr. 2005), 16(4):137-154.
Stewart; et al., "Antibiotic resistance of bacteria in biofilms", Lancet (Jul. 2001), 358(9276):135-8.
Thomas; et al., "Antibacterial activity of hydrogen peroxide and the lactoperoxidase-hydrogen peroxide-thiocyanate system against oral streptococci", Infect Immun (Feb. 1994), 62(2):529-35.
Thomas; et al., "Lactoperoxidase, peroxide, thiocyanate antimicrobial system: correlation of sulfhydryl oxidation with antimicrobial action", Infect Immun (May 1978), 20(2):456-63.
Whitaker; et al., "Rapid desensitization for non-immediate reactions in patients with cystic fibrosis", Journal of Cystic Fibrosis (Jul. 2011), 10(4):282-5.
Wolfson; et al., "Antibacterial Activity of the Lactoperoxidase System: A Review", Journal of Food Protection (Oct. 1993) 56(10):887-892.

\* cited by examiner

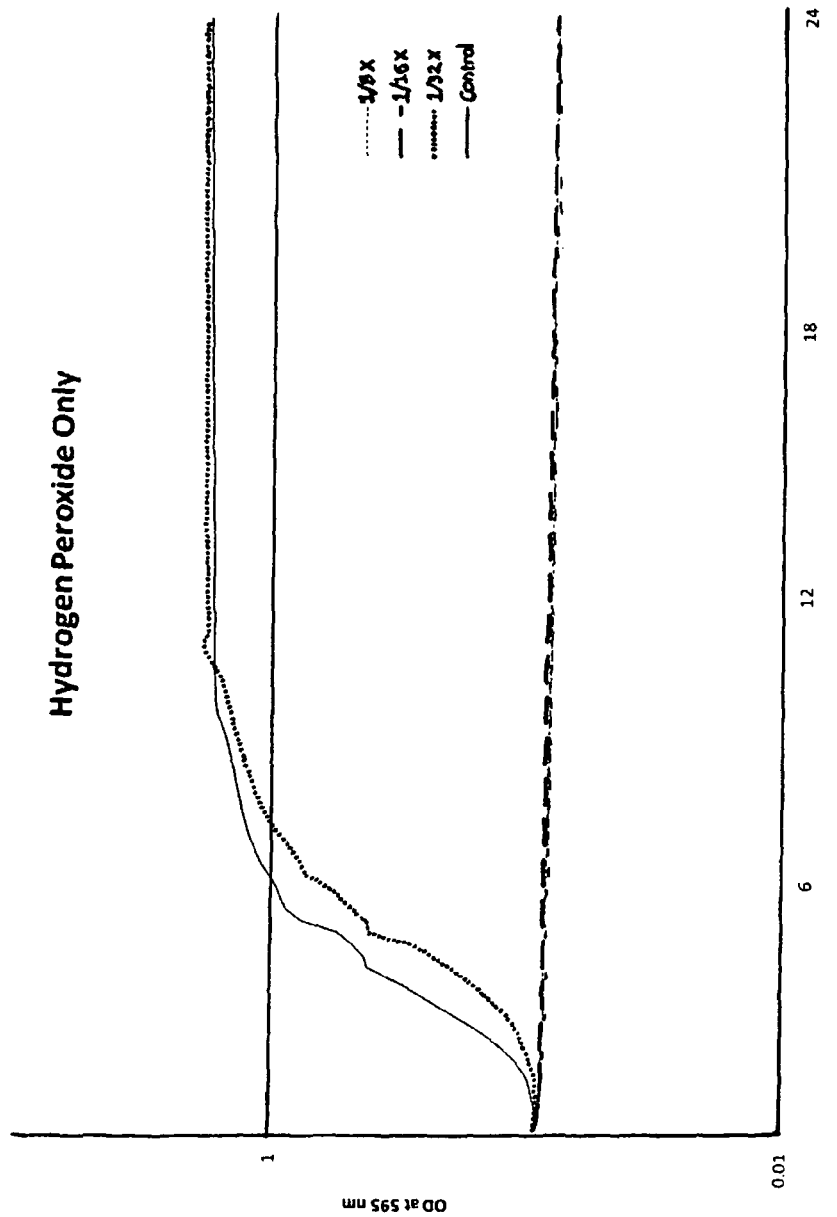
Fig 1. Susceptibility of *E. coli* to inhibition by $H_2O_2$. Growth, measured by optical density at 595 nm, was inhibited at dilutions of 1/8 and 1/16, but not 1/32.

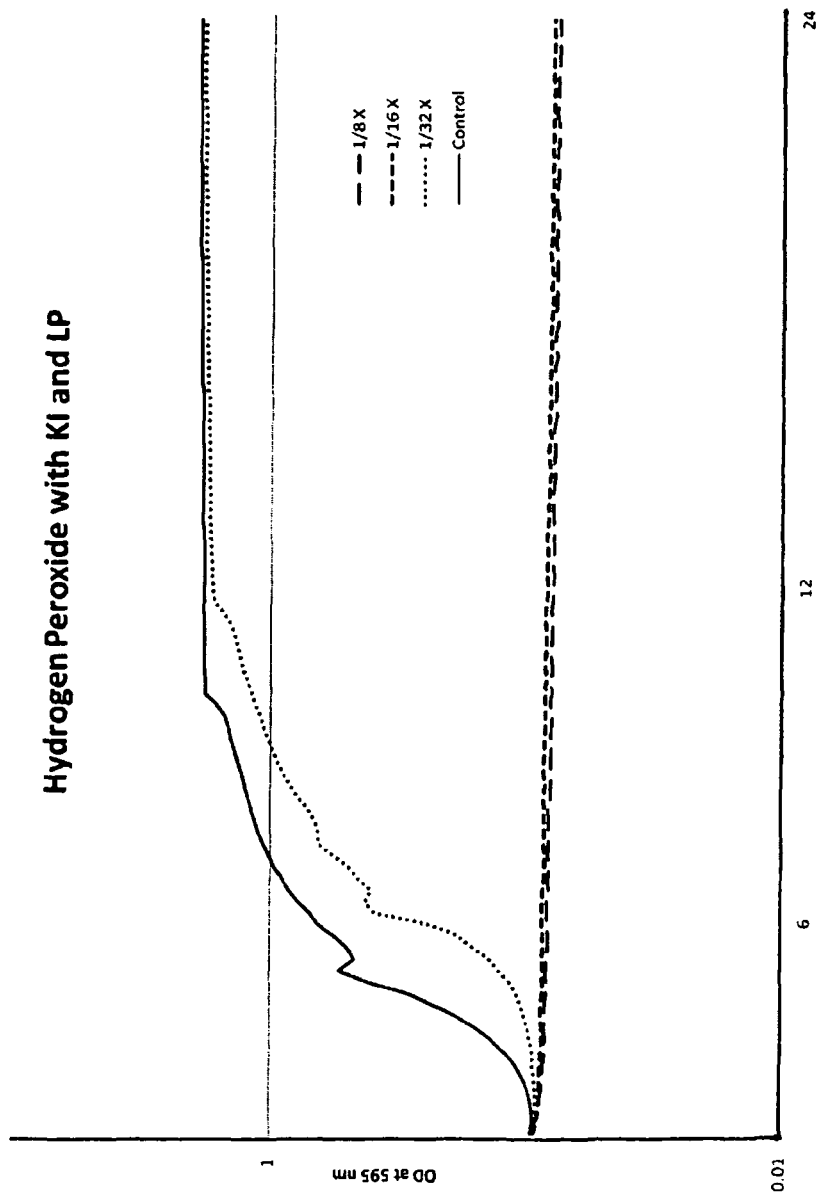
Fig 2. Susceptibility of *E. coli* to $H_2O_2$ in the presence of KI/LP. Growth, measured by optical density at 595 nm, was inhibited at dilutions of 1/8 and 1/16, but not 1/32.

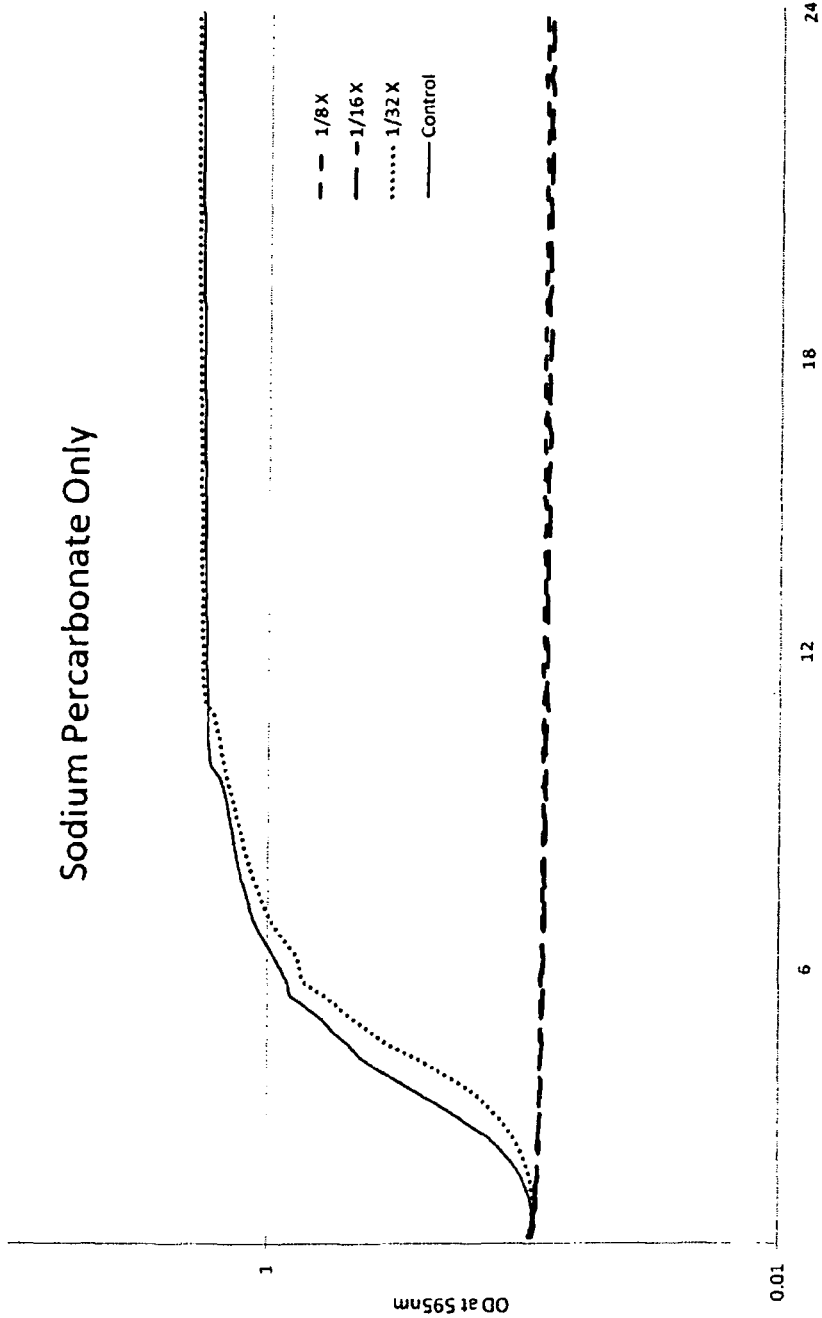
Fig 3. Susceptibility of *E. coli* to peroxide released by the addition of percarbonate. Growth, measured by optical density at 595 nm, was inhibited at dilutions of 1/8 and 1/16, but not at a dilution of 1/32.

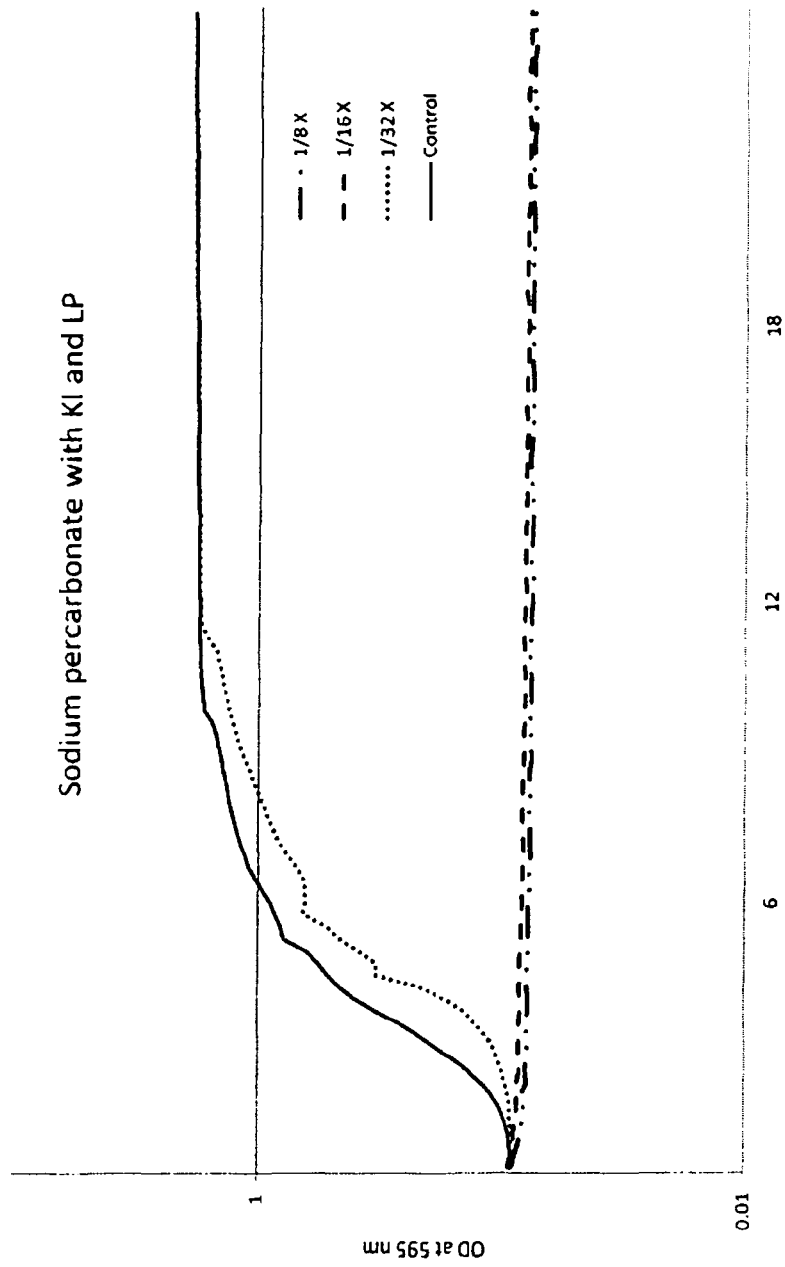
Figure 4. Susceptibility of *E. coli* to peroxide released by the addition of percarbonate in the presence of KI and LP. Growth, measured by optical density at 595 nm, was inhibited at dilutions of 1/8 and 1/16, but not at a dilution of 1/32.

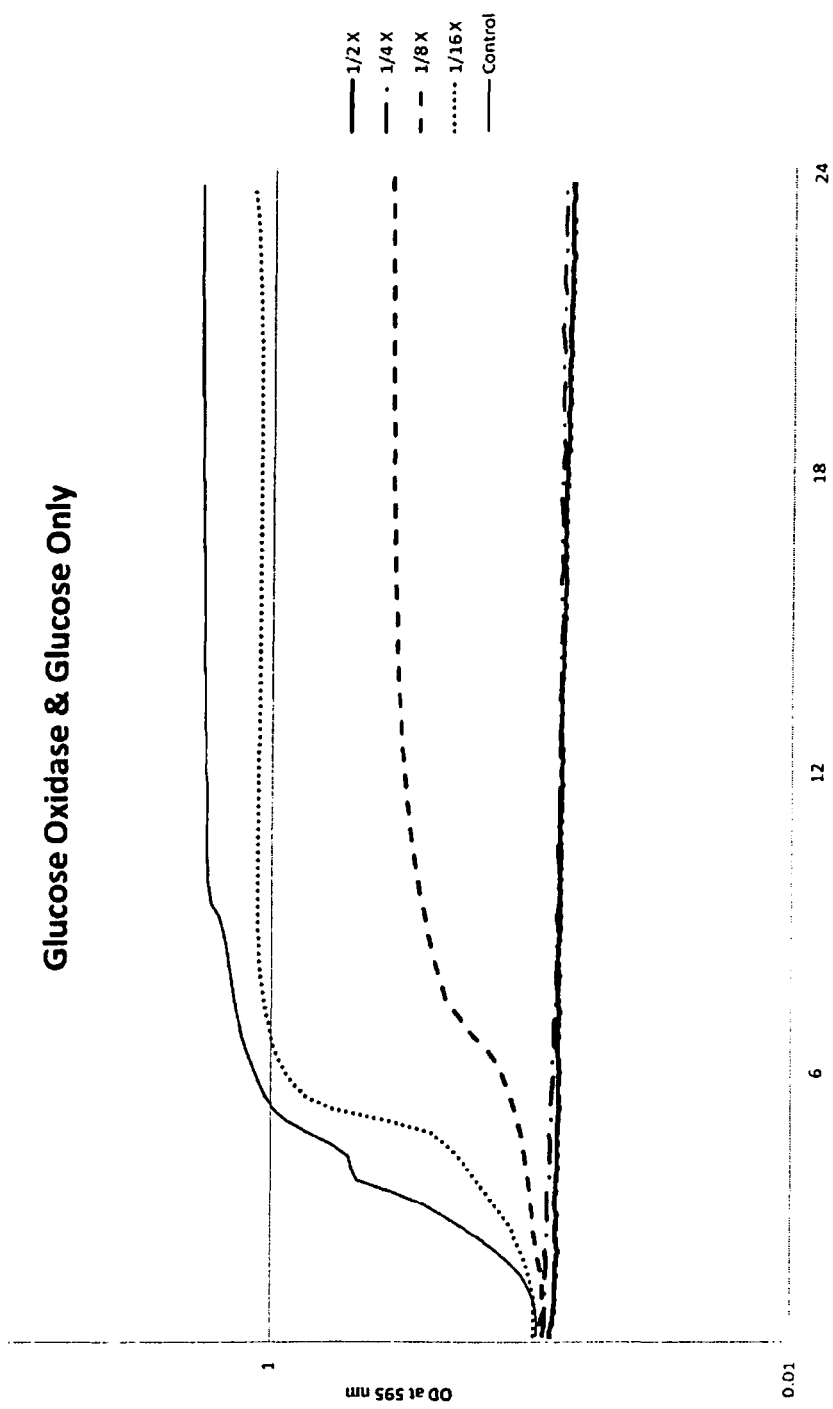
Figure 5. Susceptibility of *E. coli* to peroxide produced from Glucose by enzymatic activity via glucose oxidase.

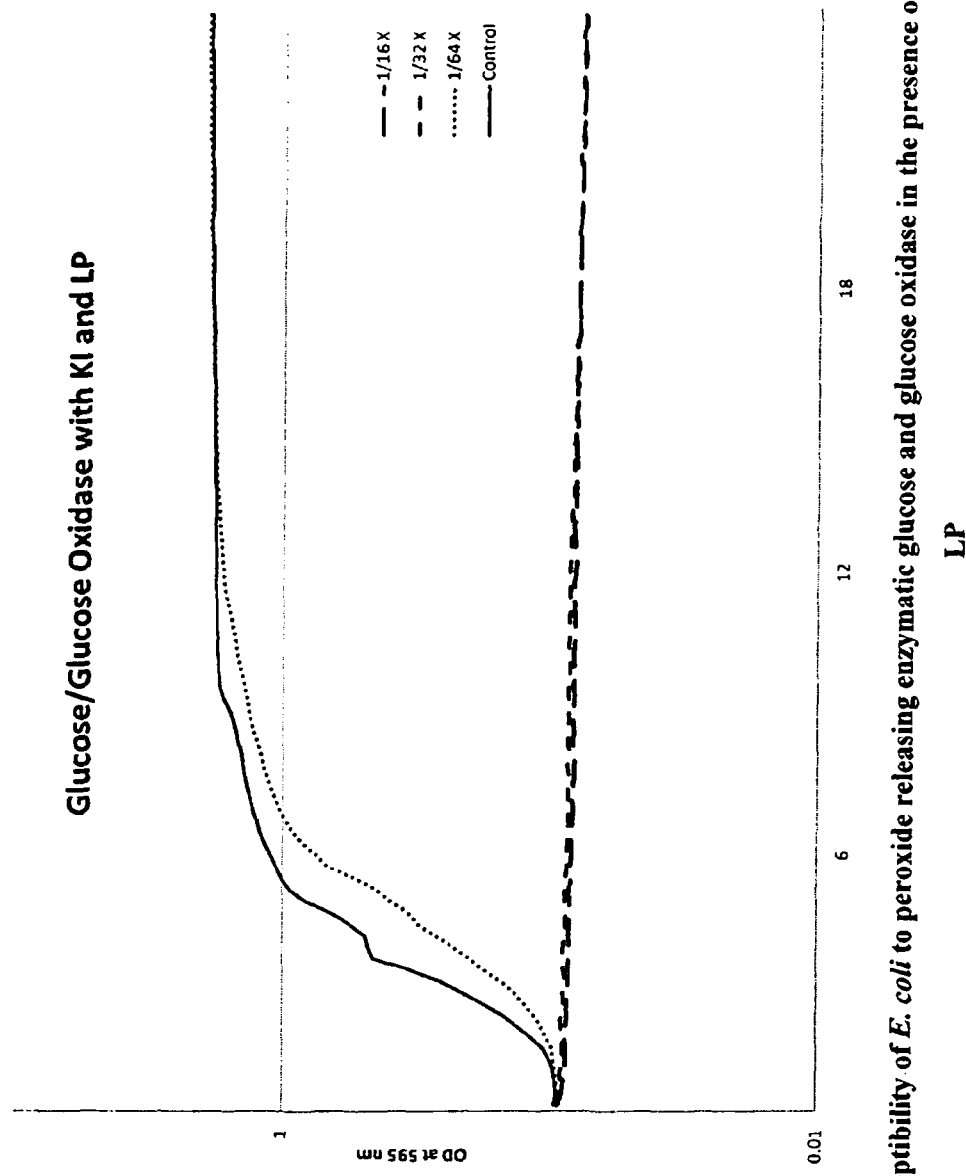
Figure 6. Susceptibility of *E. coli* to peroxide releasing enzymatic glucose and glucose oxidase in the presence of supplemented KI and LP

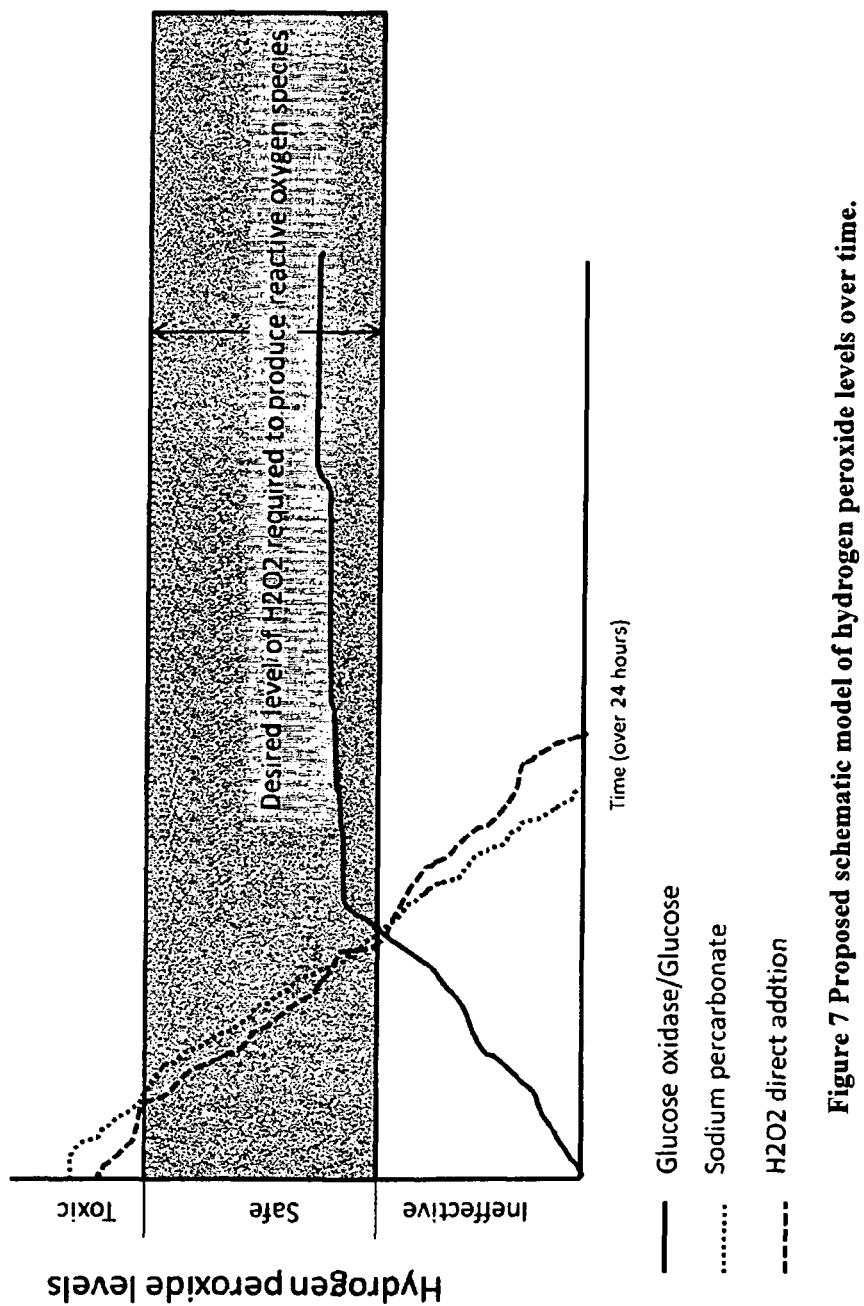
Figure 7 Proposed schematic model of hydrogen peroxide levels over time.

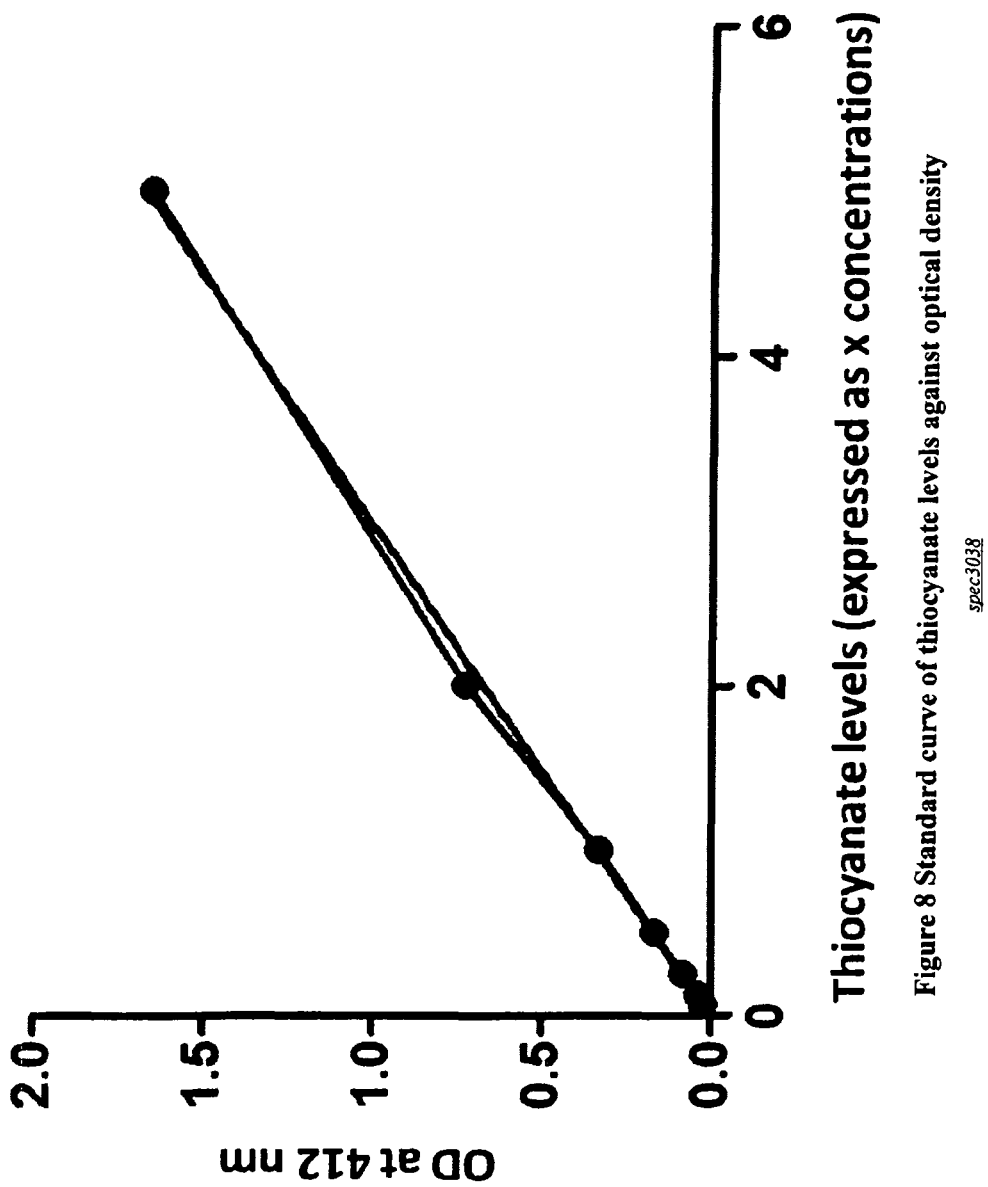
Figure 8 Standard curve of thiocyanate levels against optical density

TREATMENT OF MICROBIAL INFECTIONS

CROSS-REFERENCE TO RELATED APPLICATIONS

This application is a national stage under 35 U.S.C. 371 based on and claiming the benefit of International Application PCT/EP12/056946, filed on Apr. 16, 2012, incorporated by reference, which claims the benefit of priority from EP Application No. 11162678.4, filed Apr. 15, 2011 the entire contents of each of which are incorporated herein by reference.

FIELD OF THE INVENTION

The present application relates to an anti-microbial composition for use in the treatment of microbial infections. In particular, the composition may be used to treat bacterial infections, or for control of bacterial contamination, which avoids the use of antibiotics. Such infections include mastitis, tuberculosis, cystic fibrosis and other lung infections, and the contamination that may result from biofilm formation on surfaces such as on medical devices. However, the composition is also suitable for the treatment of viral, yeast or fungal infections or for the control of contamination by such organisms.

BACKGROUND TO THE INVENTION

Mastitis is a persistent inflammatory condition of the udder of cows and other milk-producing animals. It is one of the most common diseases in dairy cows in the United States and is also the most costly to the dairy industry. Mastitis occurs when white blood cells are released into the mammary gland, usually in response to invasion of bacteria in the teat canal. Milk from cows with mastitis has a higher somatic cell count, and the higher the somatic cell count, the lower the quality of the milk.

Normal treatment for mastitis is with antibiotics, but milk from antibiotic treated cows is not marketable, until the drug has left the cows' system. The antibiotics used may be systemic and injected into the body, or they may be forced into the teat through the teat canal by intra-mammary infusion. Mastitis can be clinical, whereby visible signs of infection are noted or sub-clinical, where the presence of infection is noted only by an increase in somatic count in the resulting milk. In some clinical situations, cows are often left untreated, though revenue is lost to the dairy farmer through a reduction in the amount of money paid for the milk, which occur where there is an elevated somatic cell count in the milk.

There are a number of other uses of the anti-microbial composition of the present invention. These include infections of the mammalian lung. Cystic fibrosis and tuberculosis are two diseases that are, at present, extremely difficult to treat. Tuberculosis symptoms are caused by infection in the lungs and require long-term antibiotic treatment. Cystic fibrosis (CF) is a condition wherein the sufferer cannot regulate the transfer of chloride ions across their membranes, particularly in the lungs. The condition invariably results in numerous, chronic, lung infections. Antibiotic treatment for either condition can lead to serious drug resistance, minimising their effectivness. At present, antibiotics are delivered through the blood stream intra-venously, or by oral suspension/tablets, or by inhalation. Drug delivery is a big problem for CF sufferers as the antibiotic cannot efficiently transverse the lung membrane to where it is required. This leads to problems wherein resistance to the drug, through the introduction of sub-inhibitory concentrations, may become a serious issue. This makes any further treatment with the drug obsolete.

Burns patients, or patients with open wounds, are extremely susceptible to bacterial infections, notably those due to *Staphlycoccal* species or *Pseudomonad* species of bacteria. Treatment of such infections will invariably be by a regimen of antibiotics, either oral or intra-venously. These may be given prophalactically, or when infection is apparent. Such use of antibiotics will often lead to resistance to the drug and an ineffective treatment outcome. The researchers envision a new method of treating burns patients with the present technology.

In addition, large numbers of antibiotic treatments each year are due to the result of medical devices that have become infected whilst in use by a patient. A large number of organisms are responsible for such infections, including both Gram-positive and Gram-negative bacteria. Infections, on such items as urinary or intra-venous catheters, are often the result of the non-sterile installation of such devices. Over the course of a number of days, any bacterial cells present on the surface of the device will proliferate, leading to the production of biofilms. Such biofilms are extremely difficult to treat with antibiotics, due to the poor transfer of the drug across to the inner cells of the biofilm mass, leading often to even greater levels of tolerance of the biofilms to the antibiotic. Infection of the medical device will often require its removal and replacement, to the discomfort of the patient. Although the infection will often be noted a number of days after installation of the medical device, it will be typically incurred as the result of bacteria being present very early in the installation.

It is generally known that a bacteriostatic effect is caused by the reaction between hydrogen peroxide and thiocyanate, catalysed by lactoperoxidase—a process referred to as the Lactoperoxidase (LP) system. In certain instances, the source of peroxide is a reaction between glucose and glucose oxidase, which results in the production of gluconic acid and peroxide. This process is used during the transport of milk. Antibacterial treatments for the control of infections have been proposed, based on the LP system. For example, PCT Application WO2008/04128 discloses a preparation with an antimicrobial and immuno-stimulatory effect, which comprises an oxidoreductase enzyme, an appropriate substrate for that enzyme to produce hydrogen peroxide, and endogenous hydrogen peroxide preparations. The preparation produces 2-stage hydrogen peroxide release; the endogenous form of peroxide ensuring that there is instantly available hydrogen peroxide and further hydrogen peroxide is produced by the oxidoreductase enzyme.

U.S. Pat. No. 6,312,687 describes a stabilised aqueous enzyme concentration comprising lactoperoxidase, glucose oxidase, an alkaline metal halide salt and a buffering agent, for use as an antimicrobial composition. U.S. Pat. No. 5,607,681 describes antimicrobial compositions, which comprise iodide anions and thiocyanate anions together with D-glucose and either glucose oxidase or glucose oxidase together with and at least one antioxidant. The composition may additionally comprise lactoperoxidase.

The proposed basis for the bacteriostatic effect of the LP system in milk is based on thiocyanate and a source of hydrogen peroxide. The thiocyanate ion is oxidised in the presence of hydrogen peroxide by lactoperoxidase, to produce hypothiocyanous acid. In certain embodiments, the peroxide ion is produced from glucose by the action of glucose oxidase rather than by using a solution of hydrogen peroxide or its release from a suitable perhydrate (such as sodium percarbonate). The present application suggests the use of further substrates to help bring about the reaction to produce hydrogen peroxide by means of supplemented enzymatic catalysis. Hydrogen peroxide is toxic to both bacterial and mammalian cells, while hypothiocyanous acid reacts with free sulphydryl groups in bacterial proteins, inactivating several metabolic enzymes.

The consensus in the literature teaches that the LP system has mainly a bacteriostatic effect on catalase positive gram positive bacteria and also that there is a pH dependent bactericidal effect on some gram negative bacteria (Wofson and Sumner, 1993, "Antibacterial activity of the lactoperoxidase system: a review" Journal of Food Protection 1993, 56(10):887-892; Kussendrager and van Hooijdonk, 2000 "Lactoperoxidase: physico-chemical properties, occurrence, mechanism of action and applications", British Journal of Nutrition, 84, Suppl. 1, S19-S25; Seifu et al., 2005 "Significance of the lactoperoxidase system in the dairy industry and its potential applications: a review", Trends in Food Science & Technology 16, 137-154). The precise mechanisms underpinning the antimicrobial properties of the LP system remain unresolved. The experimental protocols reported in the literature vary widely and many authors report bacterial inhibition, but regrowth after a particular period of time, and thus a biostatic rather than a biocidal effect (e.g. Ishido et al. "Continuous supply of OSCN− ions by lactoperoxidase system developed from lactose as the primary substrate and its anti-bacterial activities", Milchwissenschaft, 66 1, 2011) Documents have also claimed bactericidal activity using the LP system, but have reported significant numbers of culturable cells remaining after testing, even at elevated LP concentrations (e.g. Garcia-Garibay et al., 1995, Antimicrobial effect of the lactoperoxidase system in milk activated by immobilised enzymes" Food Biotechnology, (3), 157-166). As discussed elsewhere in this application, hydrogen peroxide, either provided in the medium or produced during the LP reaction, is toxic to bacterial cells and, unless specific controls are in place, it may contribute to reported antimicrobial activity. The prior art has also disclosed a range of reportedly synergistic compounds, which are claimed to either enhance, or indeed enable, the effectiveness of the LP system. In addition, US patent application number 2011/0008361 A1 suggests that the antimicrobial effect of the described extracted cationic fractions, including LP, are a combination of immune stimulation, which helps to clear infection and direct antimicrobial activity.

The lack of systematic information on the precise factors influencing the antimicrobial effects of the LP system is a barrier to commercial applications—as is the potential for hydrogen peroxide toxicity in sensitive settings, such as the mammalian lung.

While the LP system has been widely described, it is thought by those skilled in the art that this is an ineffective system to be utilised of the treatment of bacterial infection (Rainard & Riollet 2006, "Innate immunity of the bovine mammary gland", Veterinary Research 37, 369-400; Sakai et al., 2008, "Generation of hydrogen peroxide by a low molecular weight compound in whey of Holstein dairy cows", Journal of dairy Research, 75, 257-261; Sakai et al., 2008, "Production of hydrogen peroxide by a small molecular mass compound in milk from Holstein cows with high and low milk somatic cell count", Journal of Dairy Research, 75, 335-339). A lack of robust and effective bactericidal capacity of the LP and similar systems is a significant barrier to such applications. Current commercial applications based on the LP system include mouthwash, toothpaste, food preservation and disinfectants, which are mainly based on inhibition of microbial growth, rather than the killing of cells and the total elimination of bacterial populations from various settings. For example, the patents filed regarding the lactoperoxidase system (U.S. Pat. No. 4,726,945 and U.S. Pat. No. 5,607,681) are used for topical treatments and are designed mainly as a way to reduce the growth of bacteria present (either in the solutions, for example as an ionic emulsion, or acne or athlete's foot treatments, or indeed as a prophylactic in feedstuffs for animals).

The broad spectrum and numerous potential targets of the antimicrobial species of the invention are unlikely to induce the proliferation of resistance genes. Drug reactions would not be a problem either, being that components of the therapeutic composition may be produced naturally in the mammalian body (for example, via intermediates such as thiocyanate, lactoperoxidase, glucose). Reaction to drugs is a current problem, with 20% of patients reacting to B-lactam drugs ("Rapid de-sensitization for non-immediate reactions in patients with cystic fibrosis", Whitaker et al., 2011, Journal of Cystic Fibrosis, 10(4):282-5).

Ishido et al. (Milchwissenschaft, Vol. 66, No. 1, 2011) describe a lactoperoxidase system comprising lactoperoxidase, glucose oxidase and β-galactosidase, lactose and potassium thiocyanate as an agent, which is said to be antibacterial. In all cases lactose was present in the composition. The document, however, describes bacterial growth suppression only and no analysis was conducted for more than 48 hours. The document also states that there were no inhibitory effects against the gram-negative bacteria *E. coli* and *Klebsiella pneumoniae* and the gram-positive species, *S. xylosus, E. faecalis, E. faecium* and *E. raffinosus*. The results in the document are labelled as being 'growth suppression' times, the time tested being no more than 12 hours. Overall this paper thus describes a bacteriostatic effect and not a bactericidal effect.

Garcia—Garibay et al. (Food Biotechnology, 9 (3), 157-166 (1995) describes the use of β-galactosidase and glucose oxidase to produce hydrogen peroxide in raw milk, to reduce undesirable micro organisms in the milk. Again testing was conducted for 24 hours only, and thus the data presented showing a reduction in microorganism numbers indicates only a bacteriostatic effect.

Sandholm et al. (J. Vet. Med. B 35, 346-352 (1988) describes glucose oxidase for use as an antibacterial agent in teats or intramammary antiseptics.

U.S. Pat. No. 5,607,681 describes antimicrobial compositions comprising iodide and thiocyanate ions, an oxidoreductase enzyme and its corresponding oxidisable substrate, together with a lactoperoxidase. This document only describes activity against bacteria for up to 72 hours and describes no therapeutic application of the system.

The present invention represents a paradigm shift from the prior art. It describes a broad-spectrum, truly microbiocidal, therapy for treatment of infections.

The present inventors have shown that the reactive oxygen species (ROS) produced by the LP system, or by other means are, in fact, bactericidal to a wide range of pathogenic gram-positive and gram-negative bacteria, in a variety of media and across a wide range of pH and temperature ranges, based on concentration dependent dose response (see detailed description of the invention). We have also shown that the to ROS can completely kill bacteria and fungi growing in biofilms on various surfaces.

In a detailed series of controlled trials, it has been shown that this bactericidal activity can be exclusively due to the action of the ROS and that the ROS are effective in this regard with no residual hydrogen peroxide present and in the absence of any other synergistic agents such as lactoferrin, quarternary ammonium compounds, fatty acids, etc (see detailed description of the invention).

The concentrations of ROS required to completely kill particular populations of bacteria in particular settings can be calculated and used to generate precise dose response/minimum inhibitory concentration information, in a manner similar to that used for antibiotics and other antimicrobial therapeutic agents (see detailed description of the invention).

Administration of the ROS species at these dose levels can be used to completely kill a wide variety of gram negative and gram positive bacterial pathogens—including those isolated from the bovine udder and mammalian lung, those growing as biofilms attached to various surfaces; those isolated from patients; and those that are resistant to a wide range of antibiotics (see detailed description of the invention).

It has also been shown that the required bactericidal and therapeutic concentrations of the ROS species can be generated at the site of treatment, for example using the LP system in the bovine udder, or that the ROS species can be prepared externally to the site of infection and delivered in the absence of any other active ingredient to allow successful treatment and elimination of bacterial infections.

The present technology thus provides a unique way to limit microbial infection and biofilm growth on the surface of, for example, medical devices.

OBJECT OF THE INVENTION

A first object of the invention is to provide an improved composition for the treatment of microbial infections. A further object is to provide a composition which is capable of killing, as opposed to slowing the growth of, bacteria, viruses, fungi and yeasts. A still further object is to provide a composition that can kill antiobiotic resistant organisms.

Mastitis

A further objective is to provide a composition for the treatment of both clinical and sub-clinical mastitis, without the use of antibiotics. A further object of the invention is to provide a treatment for mastitis, which does not require that the milk be discarded during treatment.

A further object of the invention is to provide a clinical solution to mastitis, which would be easy to administer. Such is the reaction in the prior art discussed above, that if all the components are mixed together, the reaction would occur instantly, thus leaving a short shelf-life. In the prior art it is necessary to have two aliquots that are mixed prior to administering the product, thus starting the reaction. Another drawback is the fact that the glucose concentration is always a limiting factor. To have enough glucose in a clinical situation, a concentrated source needed to be added. This leads to solubility problems. The addition of extraneous glucose may also lead to issues in the downstream processing of the milk and may also lead to consumer problems regarding the taste and sweetness of the milk for consumption.

In an attempt to circumvent the need for glucose administration, the characteristics of milk itself were examined by the present inventors. Milk is a source of lactose. Beta-galactosidase is an enzyme that cleaves and converts the disaccharide sugar into its constituents, glucose and galactose. The use of the enzyme would therefore rely on a key constituent of milk itself to exploit the ability of the LP system to generate the reactive oxygen species at the site of infection. Using this enzyme makes it easier to administer the cocktail as the system will not react until glucose is present (and glucose would not be produced until Beta-galactosidase was in contact with the milk). This is much more useful than having to administer glucose or indeed a suitable monosaccharide or disaccharide sugar prior to usage, negating the use of a concentrated and problematic sugar solution.

Lung Infection

Another object of the invention is the treatment of a number of other bacterial infections. Drug delivery and resistance to antibiotics is a major problem in the treatment of both cystic fibrosis (CF) and tuberculosis (TB). Antibiotic resistance often occurs as a result of only sub-inhibitory concentrations of the drug reaching the target site, i.e. lungs. Chronic infections will often result from this situation, seriously impairing the health of the patient. The ideal delivery of the components of the lung would be as a nebulised spray, directly into the lungs. This would have the advantage that the components would interact directly with the organism at the correct site, and at the correct concentration. If it were administered orally or through the blood stream, greater concentrations are required to give the same effect. When using antibiotics, this will lead to large concentrations of the drug being used, increasing the chances of resistance or a reaction to the drug. Because the components of the present system are present naturally in the mammalian system (or used in feedstuffs regularly), reaction to them is highly unlikely, an advantage to treatment with antibiotics where drug reactions are common. In patients with CF, the natural level of thiocyanate is reduced in the lung due to the failure of regulation of water in the membrane, reducing the effectiveness of the naturally found lactoperoxidase system in the organ. Extraneous addition of the reactive oxygen species that could act prophylactically on people diagnosed with CF or be used to treat patients that have already developed lung infections. Such a nebulised spray has the potential to be used in hospitals in minimising infection during operations where body cavities are open to the environment and at risk, especially those caused by antibiotic resistant strains of bacteria.

Burns/Skin/Mouth

Other infections that are suitable targets for the technology are those incurred as a result of burns or an open wound. The advantage of using the described system over present antibiotic treatment regimens would be the similar to those described above in treating CF or TB as regards drug reaction, safety, efficacy, and resistance. The inventors have shown that the reactive oxygen species are effective in the treatment of biofilm based cells (those attached to a solid stratum). This would be the bacterial phenotype most noted in the lungs of TB/CF patients, and in open wounds or burns. This phenotype confers a generalised tolerance to the bacteria against a wide range of antibiotics ("Antibiotic resistance of bacteria in biofilms", Stewart & Costerton, 2001, The Lancet, 358, 135-138).

A form of the system could also serve as a general antibacterial solution, having numerous purposes. For example, a mouthwash containing the antibacterial system could help prevent the formation of biofilms within the mouth. Likewise, an antibacterial nasal rinse could be used to help alleviate sinus problems, such as sinusitis or allergic rhinitis. Currently, steroids and saline nasal washes are used. An antibacterial saline wash would, however, also help to combat bacterial colonisation within the nasal cavity.

Medical Devices

The use of reactive oxygen species, such as those generated by a haloperoxidase based system, would also hold a number of advantages in the treatment and prevention of bacterial infections on an implanted medical device. Infections (in the form of a recalcitrant biofilm) are extremely common in various devices such as catheters. A device impregnated or coated with the various enzymes would be able to react with substrates naturally present in the blood.

General Antibacterial Wash

Another object of the invention is to provide a composition for use as a generalised, safe, antibacterial wash for a multi-purpose product. The proposed system could be effective at washing/removal of bacteria from surfaces, pipes, beer lines, cooking equipment etc.

Antifungal Agent

Infections can occur as a result of yeast or fungal growth as well as bacteria. As such, a therapeutic regime capable of exerting antimicrobial activity (as opposed to antibacterial activity, as is the case with antibiotics) would be of great benefit. To this end, the antimicrobial activity of the reactive oxygen species (hypoiodate) was tested against two fungal strains of note (Example 18 below). The *Candida* strains of fungus are typically described as opportunistic pathogens. They can cause a variety of skin conditions, such as vulvovaginitis and urinary tract infections. They are prevalent in HIV patients, and other immunocompromised patients. *Saccharomyces cerevesiae* (commonly known as yeast, or bakers' yeast) is an important organism in food production. It also poses great problems for the drinks industry, and is a typical organism found on beer lines, and is the cause of beverage spoilage. As such, the antimicrobial reactive oxygen species of the invention, would be a good therapeutic candidate to treat or control fungal infections, or to clear surfaces, eradicating fungal contamination.

The invention also finds use as an anti-viral agent.

SUMMARY OF THE INVENTION

According to the present invention there is provided a microbiocidal composition comprising a reactive oxygen species or components capable of producing a reactive species, the composition being capable of delivering the reactive oxygen species to a level of at least 0.4 millimoles per litre over a 24 hour period. The composition may be capable of delivering the reactive oxygen species to a level of at least 0.5 millimoles per litre, or at least 0.6 millimoles per litre or at least 0.7 millimoles per litre or at least 0.8 millimoles per litre or at least 0.9 millimoles per litre or at least 1.0 millimoles per litre or at least 2.0 millimoles per litre over a 24 hour period.

The reactive oxygen species may be produced by the reaction of a peroxidase, a substrate for the peroxidase and hydrogen peroxide.

By microbicidal we mean a composition which is capable of killing microbes such as bacteria, viruses, fungi and yeasts, as opposed to simply retarding their growth. The microbicidal composition is capable of killing at least 90%, preferably at least 95%, more preferably at least 99%, more preferably at least 99.99%, of the microbes present in an environment to which it is applied.

The composition is also capable of killing antiobiotic resistant organisms.

The reactive oxygen species of the composition may comprise hypothiocyanate (also known as hypothiocyanite, $SCNO^-$).

The reactive oxygen species of the composition may also comprise hypoiodate ($IO^-$ also known as hypoiodite).

The reactive oxygen species of the composition may also comprise hypochlorite ($ClO^-$).

In a further aspect the invention provides a microbicidal composition additionally comprising a peroxidase enzyme and an oxidoreductase. This composition is particularly suitable for the treatment of infections in cystic fibrosis or tuberculosis patients, burns victims or patients with inserted medical devices.

In a further aspect the invention provides a microbicidal composition additionally comprising a peroxidase enzyme, an oxidoreductase, and a glycoside hydrolase. This composition is particularly suitable for the treatment of mastitis infections.

The composition may also comprise a substrate for the peroxidase.

The peroxidase may be a haloperoxidase. The haloperoxidase enzyme may be a lactoperoxidase, a chloroperoxidase, a bromoperoxidase or an iodoperoxidase. Suitable chloroperoxidases include myeloperoxidase and eosinophil peroxidase. Suitable bromoperoxidases include ovoperoxidase, vanadium bromoperoxidase and Murex snail bromoperoxidase. Suitable iodoperoxidases include horseradish peroxidase and thyroid peroxidase.

If a lactoperoxidase enzyme is used, the composition may further comprise potassium or sodium iodide or potassium or sodium thiocyanate as the substrate. Chloroperoxidase reacts with chloride ions, readily available in milk, blood or the like, so the addition of chloride ions may not always be necessary. If bromooxidase or iodooxidase are used, the substrate may be a source of bromide or iodide ions, respectively.

The haloperoxidase reacts with available hydrogen peroxide, and a suitable substrate (iodide/bromide/chloride or thiocyanate) to produce an antibacterial reactive species.

The glycoside hydrolase may be Beta-galactosidase, which converts freely available lactose in the milk into glucose and galactose.

The oxidoreductase may be glucose oxidase, which reacts with the resulting glucose to produce hydrogen peroxide. Similarly, galactose oxidase could also be used, reacting with galactose to produce hydrogen peroxide.

Preferably, the composition may further comprise a disaccharide sugar. The disaccharide could be subsequently hydrolysed by its corresponding glycoside hydrolase, for example sucrose and sucrase, allowing the release of monosaccharide sugars, which in turn could act as a source of additional hydrogen peroxide by the use of a corresponding oxireductase enzyme.

Additionally, oligosaccharides or polysaccharides containing more than two sugar molecules, and that are cleaved to produce a source of hydrogen peroxide may be added.

In some embodiments, the composition comprises two enzymes to derive a source of hydrogen peroxide; a glycoside hydrolase to break down disaccharide sugars into constituent monosaccharides, and a further oxireductase enzyme that reacts with the monosaccharide sugars to release hydrogen peroxide.

The composition may comprise additional sources of hydrogen peroxide. One additional source of hydrogen peroxide is the exogenous addition of a solution of hydrogen peroxide or its release by a suitable perhydrate, such as sodium percarbonate.

Alternatively, or in addition, a number of enzymes can be used to produce hydrogen peroxide. Xanthine oxidoreductase/oxidase reacts with either hypoxanthine or xanthine (both present in milk) to produce hydrogen peroxide. Therefore, xanthine oxidoreductase/oxidase and/or xanthine could be added to the composition producing hydrogen peroxide. Similarly, sugar alcohols can be reacted with their appropriate oxidase enzymes to produce a source of hydrogen peroxide. For example, glycerol oxidase reacts with glycerol to produce a source of hydrogen peroxide and, therefore, glycerol oxidase/glycerol could be added to the composition. Another example would be mannitol reacting with mannitol oxidase. Further to this, citric acid is known to release hydrogen peroxide, and therefore could also be added to the composition. Similarly, L-amino acid oxidase is an enzyme that reacts with free amino acids (also present in milk) to produce hydrogen peroxide. Likewise, its addition (with or without L-amino acid supplementation) could provide a source of hydrogen peroxide.

The aspect of the invention, which provides a bactericidal composition additionally comprising a peroxidase enzyme, an oxidoreductase, and a glycoside hydrolase (specifically Beta-galactosidase), has proven to have extremely effective antibacterial qualities in milk. In particular, the system is effective at completely killing both Gram-positive and Gram-negative organisms at high levels of bioburden (i.e. eliminating $10^{8-10}$ cells/ml). Based on the prior art, this is a surprising finding as the WHO have stated that the lactoperoxidase system 'exerts primarily a bacteriostatic effect in raw milk' and was suitable only for limiting bacterial growth on a short term basis by such a means during the transport of raw milk, in the absence of refrigeration (Report of an FAO/WHO Technical Meeting FAO Headquarters, Rome, Italy, 28 Nov.-2 Dec. 2005). Other researchers concluded that any bacteriocidal activity in the system was due to the hydrogen peroxide component and that the lactoperoxidase system was bacteriostatic (Thomas et al., 1994, "Antibacterial activity of hydrogen peroxide and the lactoperoxidase-hydrogen peroxide-thiocyanate system against oral streptococci", Infection and Immunity, Vol. 62, No. 2, p 529-535).

The Beta-galactosidase reacts with lactose present in milk, to produce glucose and galactose. The resulting glucose reacts with the glucose oxidase to produce hydrogen peroxide. The hydrogen peroxide reacts with potassium iodide/thiocyanate to produce an antibacterial effect. The antibacterial effect is aided by lactoperoxidase which catalyses the peroxidation of iodides and other suitable substrates.

Relying on the inherent lactose in milk negates the use of a highly concentrated glucose solution, which was a limiting factor in an in vitro situation, making it possible to use the product in the field.

In another aspect of the invention, there is provided a composition for the treatment of infections or contamination, comprising Xanthine oxidoreductase/oxidase. The composition may further comprise either hypoxanthine or xanthine or both. The composition may also comprise an oxidoreductase or a glycoside hydrolase or disaccharides.

In yet another aspect of the invention there is provided a composition for the treatment of infections or contamination comprising L-amino acid oxidase. The composition may further comprise free amino acids. The composition may also comprise an oxidoreductase or a glycoside hydrolase or disaccharides.

One potential of the composition of the invention lies in the treatment of bovine (or other mammal) mastitis. It could be used to treat both clinical and sub-clinical mastitis and would provide the advantage of not requiring the removal of resulting treated milk from the bulk pool. The enzymes present in the proposed solutions are safe and the potential substrates, including potassium iodide or thiocyanate are safe at the concentrations used. The composition is unlikely to induce resistance to antibiotics, which is an additional advantage. In addition, the report of an FAO/WHO technical meeting in Rome, Italy on 22 Nov.-2 Dec. 2005 indicated that a lactoperoxidase system does not introduce substances into milk that are not normal metabolites.

The use of enzymes to produce the biocidal reactive oxygen species of the invention, provides the means to continuously produce the composition over periods of time, which is advantageous when compared to antibiotic treatments, where new molecules must be externally added to replenish the antimicrobial activity.

One product suitable for the treatment of mastitis is an intramammary infusion delivery device (optionally presented as a dual barrelled syringe) loaded with 7-10 ml solution (increasing its viscosity by gelatine supplementation) containing 2 mg glucose oxidase (~200 units/mg), 0.5 ml Beta-galactosidase ($\geq$2,600 units/ml), 4 mg lactoperoxidase ($\geq$80 units/mg), and 100-150 mg potassium iodide, to be used to generate the bactericidal reactive oxygen species to treat mastitis.

Other preparations could hold the enzymes as a lyophilized powder to be mixed with a solution of substrates prior to use, thus aiding shelf-life of the reaction where refrigeration is not a possibility. Other similar products may be produced based on the weight of animal (sheep, etc.), milk production, and the bioburden level in the infected udder. Further to this, various combinations of components could also be prepared, notably using bromide/thiocyanate instead of iodide, using a different oxidoreductase enzyme, or the supplementation of different possible sources of hydrogen peroxide, or to use a xanthine oxidoreductase (a complex enzyme which comprises xanthine oxidase) or an L-amino acid oxidase (a member of the oxidoreductase enzyme family) approach. An alternative product involves substitution of lactoperoxidase with any other enzyme that reacts with hydrogen peroxide and suitable substrate to produce the antimicrobial species. Of these, chloroperoxidase is suitable with a loading of 7-10 ml solution (increasing its viscosity by gelatine supplementation) containing 2 mg glucose oxidase (~200 units/mg), 0.5 ml Beta-galactosidase ($\geq$2,600 units/ml), and 50 µl chloroperoxidase ($\geq$11, 100 units/ml).

A lactoperoxidase system has been described before (U.S. Pat. Nos. 4,726,948 and 5,607,681) in a number of formulations. The World Health Organisation (Report of an FAO/WHO Technical Meeting FAO Headquarters, Rome, Italy, 28 Nov.-2 Dec. 2005) has recommended its use as a method of increasing the longevity of milk in the absence of refrigeration in $3^{rd}$ world countries. The WHO recommended a system using sodium percarbonate as the source of hydrogen peroxide. The aspect of the invention presented here differs from the known LP system in that it uses an alternative source of hydrogen peroxide, provided by the sequential cleavage of lactose present in the milk. Further to this, an alternative is to use chloroperoxidase enzyme in place of lactoperoxidase, wherein, it reacts with salt already present in milk, negating the need for halide supplementation to the udder. Either form of this aspect of the invention (lactoperoxidase/chloroperoxidase) offers the advantage over existing preparations in that they would not start reacting until administered to the udder. Each would have a lengthy shelf-life at 4° C. The WHO discussed a number of problems in their described incarnation of the LP system that would not occur in the aspect of the invention described herein. The system proposed by the WHO delivered thiocyanate and percarbonate powders in sachet form to milk. Powdered thiocyanate is hygroscopic and may degrade overtime, and sodium percarbonate as a source of hydrogen peroxide may lead to oxygen production, which could cause rupture and breakage of the sachet.

The invention described here improves on the lactoperoxidase system described by Kussendrager and van Hooijdonk, 2000 (Lactoperoxisdase: physico-chemical properties, occurrence, mechanism of action and applications. British Journal of Nutrition, 81, 519-525). When treating mastitis, it uses a key ingredient of milk itself, lactose, to drive the reaction to produce the specific required concentrations of the bactericidal reactive oxygen species to eliminate the infection. The supplementation of two enzymes (Beta-galactosidase and glucose oxidase) as opposed to sodium percarbonate, allows a slow, prolonged, release of hydrogen peroxide necessary to allow continuous production of the bactericidal agents at a controlled level. Because of the availability of lactose in the proposed environment, hydrogen peroxide would not be a limiting factor in the reaction. A relatively small amount of Beta-galactosidase has proved just as effective as larger volumes of glucose supplementation.

The invention improves on the lactoperoxidase system found naturally in mammals as it regulates the levels of hydrogen peroxide present (and indeed any other components). During a typical infection, the level of hydrogen peroxide is quenched by bacterial catalase activity, thus reducing the effectiveness of the system. The low availability of hydrogen peroxide has lead a number of researchers to believe the antimicrobial nature of the lactoperoxidase system was 'questionable' (Rainard & Riollet 2006, "Innate immunity of the bovine mammary gland", Veterinary Research 37, 369-400; Sakai et al., 2008, "Generation of hydrogen peroxide by a low molecular weight compound in whey of Holstein dairy cows", Journal of dairy Research, Journal of Dairy Research, 75, 257-261; Sakai et al., 2008, "Production of hydrogen peroxide by a small molecular mass compound in milk from Holstein cows with high and low milk somatic cell count", Journal of Dairy Research, 75, 335-339).

The embodiment of the invention which uses xanthine oxidoreductase/oxidase or L-amino acid oxidase as sources of hydrogen peroxide would improve the technology as neither require sugar supplementation, use constituents of the milk itself, and do not alter the taste of the milk as regards its sweetness.

The patents filed regarding the lactoperoxidase system (U.S. Pat. No. 4,726,945 and U.S. Pat. No. 5,607,681) are used for topical treatments and are designed mainly as a way to reduce the growth of bacteria present (either in the solutions, for example as an ionic emulsion, or acne or athlete's foot treatments, or indeed as a prophylactic in feedstuffs for animals). The present invention provides a novel means to treat "full-blown" bacterial infection as an alternative to antibiotic regimens. High levels of bactericidal activity have been shown using the invention, in its various aspects, both at an in vitro and in vivo level.

Variations on the technology, namely the type of enzymes and substrates utilised to produce the bactericidal reactive oxygen species, would be used to treat other types of bacterial infection.

An antimicrobial nasal rinse product in accordance with the invention contains the required components of the system. These include a suitable peroxidase enzyme, such as lactoperoxidase or chloroperoxidase, the appropriate substrate (such as iodide, thiocyanate, or chloride ion). Similarly, a source of hydrogen peroxide would be supplied, optionally by a mono-saccharide sugar and its cleaving enzyme, for example glucose and glucose oxidase, or a hydrogen peroxide releasing molecule, such as percarbonate or citric acid. These components and substrate(s) may be supplemented as a dry salt powder/lyophilised enzyme in a sachet that would be re-hydrated before use. The use of saline solution (or the addition of extra sodium chloride to the sachet) would regulate the required salinity. Likewise, the use of sodium bicarbonate would regulate the acidity. A dry-powdered form of the system would allow the product to maintain shelf-life, reduce the volume of the product so that only water would be needed to 'activate' the system.

A composition for the treatment of CF/TB may be a solution delivered to the lung by means of a nebulised spray, which would deliver the required components of the invention (either lactoperoxidase or chloroperoxidase, required substrate (thiocyanate/chloride), and a source of hydrogen peroxide (glucose and glucose oxidase, or other possible enzymatic methods, such as xanthine oxidoreductase/oxidase and hypoxanthine/xanthine or L-amino acid oxidase and L-amino acids, or by the addition of a perhydrate such as sodium percarbonate, or even by the direct addition of a hydrogen peroxide solution) to the lung. Storage of the solution may be achieved by separating certain components to ensure the reaction would only occur on delivery to the lung. As such, one solution may contain the haloperoxidase enzyme and glucose and would be mixed with another solution containing the substrate and glucose oxidase. Mixing of these would start the reaction, producing the highly antibacterial reactive species that could be delivered to the lung by nebuliser in a given volume.

Concentrations of each of the components may be tailored to the human lung, but would be of the same possible order of magnitude as those described for the mastitis treatment above. Likewise, the same overall delivery mechanism may be used for a general antibacterial throat spray, which would not require the need for nebulisation.

The ability to efficiently eradicate biofilm cells by the present invention (see detailed description of the invention Example 3) confers a significant improvement over presently used antimicrobial treatments that are known to be inefficient in the treatment of cystic fibrosis infection of the lung as *Pseudomonad* strains exhibit greater tolerance to antibiotics ("Differences in biofilm formation and antimicrobial resistance of *Pseudomonas aeruginosa* isolated from airways of mechanically ventilated patients and cystic fibrosis patients", Fricks-Lima et al., 2011, International Journal of Antimicrobial Agents, 37(4), 309-315).

One embodiment of the invention also provides a new method of treating burns patients. A poultice impregnated with the enzymes capable of producing the antimicrobial species (notably a haloperoxidase; such as lactoperoxidase/chloroperoxidase; and an oxidoreductase, such as glucose oxidase) may be dipped into a gel based solution containing ingredients necessary for the production of antibacterial compounds; the potential substrate, notably iodide/thiocyanate/chloride; and a monosaccharide sugar that will react with the oxidoreductase enzyme, notably glucose. This poultice could be placed over the wound where required, allowing a safe release of highly antibacterial compounds, maintaining a safe, aerobic environment needed for tissue repair.

Concentrations of the components would again be similar to those described above for the treatment of mastitis.

Alternative methods of producing hydrogen peroxide could be used by the varying of the oxidoreductase and sugar, by other enzymatic reactions (L-amino acid oxidase and L-amino acids, xanthine oxidoreductase/oxidase and xanthine/hypoxanthine), by the addition of a perhydrate such as sodium percarbonate, or the direct addition of a solution of hydrogen peroxide.

The embodiment of the invention utilising the haloperoxidase based system may also be employed to improve the physical properties of medical devices, to limit the chance of causing infection during implantation into a patient. The method is safe, limiting drug reaction or resistance, as is often the case in using antibiotics. The impregnation of required enzymes, lactoerpoxidase or chloroperoxidase, and an oxidoreductase, glucose oxidase and/or additional substrates, onto the surface of the device, is a viable method of delivery. Typically, the substrates required to drive the reaction, notably glucose and thiocyanate/chloride are present in blood, saliva, milk, and urine, thus a reaction would occur on the slow release of the enzymes and/or additional substrates. The slow release of the enzymes may be undertaken by their anchoring/coating on the surface by means of electrical charge, in the form of an impregnated biodegradable polymer. As the polymer degrades, fresh enzyme molecules are free to react with substrates passing over the device. The steady release of these enzymes over the course of the initial number days, post implantation, would maintain sterility of the device in the important window of opportunity where infections/biofilms would normally take hold.

A generalised antibacterial solution may be produced by the mixing of two solutions (or possibly their dried-powder forms in water). For example, an antibacterial solution may be prepared by the mixing of crude sources of peroxidase enzyme (chloroperoxidase or lactoperoxidase, for example), the appropriate substrate (optionally in the form of a salt for example sodium iodide/thiocyanate/or chloride) and a source of hydrogen peroxide (cheap sources would include citric acid, percarbonate, hydrogen peroxide itself, or sugars with the appropriate enzyme to react with it—for example, glucose and glucose oxidase). This aspect on the invention would be activated by the mixing of the components in solution. The solution may be delivered to the surface needing to be cleaned. Such examples would include beer lines, ceramic surfaces, metal surfaces, etc. and could be used in hospitals, factories, kitchens and the like. The solution would be relatively non-toxic, and would not produce the odour associated with many cleaning products such as bleach. Further to this, a protein such as lactoferrin could be supplemented to the system to increase potency. Lactoferrin is known to help break down bacterial biofilm, and thus may serve to accentuate the antimicrobial nature of the product.

Likewise, the proposed compositions could be pre-prepared or activated before administration to an infection site.

DETAILED DESCRIPTION OF THE INVENTION

EXAMPLE 1

An antimicrobial composition was produced by the addition of 150 mg potassium iodide, 4 mg lactoperoxidase (≥80 units/mg), and 2 mg glucose oxidase (~200 units/mg) to 7 ml sterile water. This embodiment is referred to as 'KI-Dose-150'. Similarly, a composition was prepared using 150 mg potassium thiocyanate, and is referred to as Thio-Dose-150'.

The antimicrobial properties of these compositions were tested using a doubling dilution 96-well plate growth assay-based method. An aliquot of the composition was added to 150 µl growth medium (with 1-2% glucose present) containing $10^{7-8}$ bacterial cells, and brought to a final volume of 300 µl. The composition concentration was doubly diluted by the removal of 150 µl of the mixture and transfer to the next well containing 150 µl of identical growth medium, lacking the ROS producing components. The optical density of the medium was measured for 24 hours at 595 nm. The concentration required to completely inhibit the bacteria was the lowest concentration of the composition employed that resulted in no visible signs of growth in the medium after the 24 hours. Controls included wells to which none of the composition was supplemented, or wherein, one of the components was removed from the composition. This method was used to determine the antimicrobial potency of the compositions against a variety of micro-organisms, notably *Escherichia coli, Staphylococcus aureus, Psuedomonas aeruginosa, Burkholderia cepaciae, Streptococcus dysglactiae, Streptococcus uberis*, a non-haemolytic coliform. These organisms are the often described as causative agents of numerous infections, notably bovine mastitis, cystic fibrosis lung infections, skin infections, burns infections, etc and, as such, represent the variety of organisms that the composition will be used to treat. The relative susceptibility of the organisms to the compositions is described in Table 1 (Ratio indicates the lowest dilution of the composition at which no growth was still recorded, for example, 1:800 had the composition diluted to the equivalent of 1 µl composition for every 800 µl of growth medium) and are the lowest concentrations of the composition that inhibited growth. The estimated level of the antimicrobial reactive oxygen species (ROS) produced over the course of 24 hours is also provided (see also Example 19 below).

TABLE 1

Susceptibility of bacterial strains to 'Thio-Dose-150' and 'KI-Dose-150'. The MIC indicates the level of reactive oxygen species below which bacteriocidal effects were not noted (millimoles per litre produced over 24 hours).

|  | Thiocyanate | | Iodide | |
| --- | --- | --- | --- | --- |
| Strain | Dilution | ROS MIC | Dilution | ROS MIC |
| E. coli ATCC 25922 | 1:400 | 0.4-0.8 | 1:800 | 0.25-0.5 |
| Strep. dys 143 | 1:48,000 | 0.003-0.007 | 1:48,000 | 0.005-0.01 |
| Strep. dys 160 | 1:48,000 | 0.007-0.01 | 1:48,000 | 0.005-0.01 |
| Strep. uberis | 1:24,000 | 0.00-0.01 | 1:24,000 | 0.005-0.01 |
| Staph. aureus 15676 | 1:800 | 0.3-0.6 | 1:800 | 0.25-0.5 |
| Burk. cepacia | 1:800 | 0.3-0.6 | 1:1,600 | 0.075-0.15 |
| P. aeruginosa PA01 | 1:800 | 0.3-0.6 | 1:1,600 | 0.075-0.15 |
| Non-haemolytic coliform | 1:400 | 0.4-0.8 | 1:800 | 0.25-0.5 |

EXAMPLE 2

The lactoperoxidase system has been discussed in terms of its bacteriostatic or inhibitory qualities. The protocol described in Example 1 was performed in larger scale volumes (an initial 500 µl aliquot of KI-Dose-150 or Thio-Dose-150 was added to 10 ml growth medium containing the test organism and doubly diluted). After 48 hours of incubation, the bacteriocidal qualities of the system were investigated by the sub-culuture of the inoculated broths to agar plates. The composition was deemed to be bacteriocidal for a bacterial strain at a particular concentration if no more than 0.0001% of cells were recoverable after 24 hours following sub-culture to the fresh agar plate (ie 72 hours after exposure to the antimicrobial composition). The compositions were bacteriocidal to each of the tested strains at concentrations that would be achievable for an infection treatment (lowest dilutions at which inhibition was noted are presented in Table 1 above.

EXAMPLE 3

The choice of hydrogen peroxide source can be shown to affect the LP system and also the ability to produce an antimicrobial composition based on ROS at bactericidal concentrations. Aliquots (20 ml) of nutrient broth were inoculated with $10^8$ cells of $E.$ $coli$ ATCC 25922, and 150 µl of the inoculated broth were added to wells in a 96 well growth plate. This was repeated with the inoculated broth being further supplemented with LP (37.5 µl of a 4 mg/ml solution) and KI (75 µl of a 40 mg/ml solution) to the medium.

Sources of hydrogen peroxide were added (150 µl) to well 1 and doubly diluted to well 11, but not to well 12, which acted as a control. The sources of hydrogen peroxide were as follows:

5 ml water containing 40 µl $H_2O_2$ (30% w/v)
5 ml water containing 50 mg sodium percarbonate
5 ml glucose (20%)+47 µl glucose oxidase (2.5 mg/ml, 200 Units/mg)

FIG. 1 illustrates that 1:8 and 1:16 dilutions of the $H_2O_2$ solution were inhibitory to $E.$ $coli$, though the 1:32 dilution was not. Repetition of this assay in the presence of supplemented KI and LP did not accentuate the effects observed using $H_2O_2$ directly, with a 1:32 dilution still not inhibitory to the bacteria (FIG. 2), although the levels of $H_2O_2$ would have been significantly reduced during the incubation, in this case. This is because the supplemented LP would use available peroxide to catalyse the production of reactive oxygen species using the supplemented KI as substrate.

The pattern of inhibition caused by the addition of the sodium percarbonate solution to inoculated broths (FIG. 3) was identical to that observed following direct $H_2O_2$ addition. It is clear that there was no difference as regards inhibition, following supplementation of KI and LP when using sodium percarbonate as the source of hydrogen peroxide (FIGS. 3 and 4) although the peroxide would have been used to produce the less toxic reactive oxygen species, hypoiodate, during the incubation.

It was clear that only a 1:2 and 1:4 dilution of the glucose/glucose oxidase solution added produced sufficient $H_2O_2$ to be inhibitory (FIG. 5), but not at dilutions of 1:8 (partial), 1:16 or 1:32. It was clear, however, that on repetition of the glucose/glucose oxidase assay in the presence of the KI and LP (FIG. 6), inhibition of $E.$ $coli$ occurred at a much greater dilution (up to and including a 1:32 dilution) than achievable in the absence of added KI and LP (FIG. 5).

This result clearly indicates that the enzymatic production of hydrogen peroxide at levels greatly lower than those that are inhibitory to bacteria are sufficient to drive the production of inhibitory concentrations of antimicrobial reactive oxygen species. This offers a method to deliver a therapeutic dose of the antimicrobial reactive oxygen species without accumulation of potentially toxic $H_2O_2$.

EXAMPLE 4

Volumes of milk (10 ml) were inoculated with $E.$ $coli$ and supplemented with the lactoperoxidase, glucose oxidase, potassium iodide and Beta-galactosidase as a mechanism to generate the antimicrobial composition of the invention. Concentrations of 3.75 mg/L glucose oxidase (~200 units/mg), 12 mg/L lactoperoxidase (≥80 units/mg), 120 mg/L potassium iodide/thiocyanate, and 400 ml/L Beta-galactosidase (≥2,600 units/ml) or greater were sufficient to observe antibacterial activity. At the optimised concentrations these mixtures proved lethal to up to $10^8$ cells/ml of $E.$ $coli$ (subculture of the solution to fresh agar plates resulted in no recoverable cells.). Concurrent negative controls (excluding each of the components) resulted in an increase of bacterial numbers over the proceeding 24 h in the milk. The composition, generated in this manner, worked efficiently in the first 2 hours to eradicate bacteria.

A preparation was designed for use in the treatment of bovine mastitis by an intramammary infusion method. A field trial (6 cows, 6 quarters) was conducted wherein cows were treated on 4 occasions post milking with the proposed bactericidal composition produced by an enzymatic system (in this case, using Beta-galactosidase milk activation as an object of the present invention). The preparation contained lactoperoxidase (4 mg≥80 units/mg), glucose oxidase (2 mg, ~200 units/mg), Beta-galactosidase (0.4 ml, ≥2,600 units/ml), and potassium iodide (150 mg) per dose. Significant decreases were noted in somatic cell counts of the animals as a result of treatment, recorded between 5 and 30 days after treatment. Results from the trial are tabulated below (Table 2), farms C and D.

TABLE 2

Somatic Cell Counts of treated animals.

| Cow # | Initial SCC (in millions) | After 5 days | 30 days | % Reduction |
|---|---|---|---|---|
| Farm C | | | | |
| 1 | 8.9 | | 1.46 | 84 |
| 2 | 11.58 | | 0.36 | 97 |
| 3 | 2.32 | | 0.647 | 72 |
| Farm D | | | | |
| 118 | 11.094 | 1.234 | | 89 |
| 529 | 24.942 | 18.278 | | 27 |
| 207 | 22.835 | 4.214 | | 82 |

An attempt was made to determine the effects of the milk pasteurisation process on the enzymatic components, which can be used to produce the reactive oxygen species of the composition of the present invention. Working concentrations of the enzymes were heated in 50 µl volumes to 72° C. and held for 15, 30, 60, 300 or 600 seconds.

Appropriate concentrations of these aliquots were then transferred to milk containing the necessary components of the system and ~$10^8$ cells/ml $E.$ $coli$. Total viable counts were performed after 24 hrs incubation at 37° C. This allowed the determination of whether the enzymes were still active after heating. Glucose oxidase demonstrated activity after 300 seconds heating, as did lactoperoxidase. The activity of Beta-galactosidase was, however, impaired by the heating process, with a typical pasteurisation cycle (72° C. for 15 seconds) completely inactivating the enzyme. This would suggest that bacterial starter cultures used in post-processing of milk (yogurt and cheese) would not be inhibited by the use of the described preparations to generate the reactive oxygen species of the present invention.

A 10 ml volume of milk was used a model to test the hypothesis that a chloroperoxidase enzyme could be used instead of lactoperoxidase to generate antimicrobial reactive oxygen species. Milk was again spiked with E. coli (~$10^7$ cells/ml). A suitable concentration of both Beta-galactosidase (2-3 µl, ≥2,600 units/ml) and glucose oxidase (15 µl of a 2.5 mg/ml solution, ~200 units/mg) was supplemented to the milk. A preparation of chloroperoxidase (0.5 µl, ≥11,100 units/ml) was then added, and resulted in a complete eradication of E. coli cells within 24 hours, at 37° C. Control experiments, without each, or two of the enzymes, resulted in the proliferation of a bacterial numbers within the same incubation conditions ($10^{8-9}$ cells/ml).

EXAMPLE 5

A field trial was conducted using a supplemented glucose based enzymatic system to produce the reactive oxygen species and to assess the efficacy of such an approach to producing the antimicrobial agents. A number of cows (8) were treated twice a day for two days with the supplied system. These cows demonstrated a marked decrease in their somatic cell counts (in the region of 50% after 5 days, see Table 3, Farms A and B, followed by a similar decrease after a further 5 days for Farm B, where subsequent data was available), a proxy method of measuring bacterial load. This demonstrated the efficacy of the lactoperoxidase system in generating the antimicrobial species, without use of Beta-galactosidase, to give assurance that it was a feasible source for generation of the bactericidal species.

TABLE 3

Somatic Cell Counts of treated animals using a glucose supplementation system to produce the antimicrobial reactive oxygen species.

| Cow # | Initial SCC (in millions) | After 5 days | 10 days | % Reduction |
|---|---|---|---|---|
| Farm A | | | | |
| 438 | 3.016 | 1.68 | | 42.3 |
| 852 | 6.981 | 3.476 | | 50.2 |
| 892 | 1.56 | 0.516 | | 66.9 |
| 717 | 6.331 | 0.218 | | 96.6 |
| Farm B | | | | |
| 794 | 3.4 | 0.926 | 0.59 | 82 |
| 501 | 0.71 | 0.47 | 0.394 | 44.5 |
| 831 | 3.5 | 3.3 | 0.995 | 71 |
| 823 | 0.812 | 0.554 | 0.186 | 77 |

EXAMPLE 6

A trial was conducted to determine the ability of the proposed composition to eradicate biofilm-based bacterial cells. This was performed using two culturing techniques. A continuous culture of E. coli was established using a chemostat. This system is designed to allow the operator the ability to control the growth rate of the organism. Most infections will occur as a result of slow growing cells (due to limited nutrient availability). This phenotype will have an effect on the tolerance of cells to antimicrobials, and is more realistic of the host environment. Further to this, these cultures were used to grow biofilms on a Modified Robbins Device, wherein the cells were allowed to attach and proliferate on the surface of a polyurethane coupon. These cells share the phenotype of biofilm cells noted in a typical infection in mastitis, CF/TB lungs, wounds, burns, and on medical devices and respond in a similar fashion and offer a viable model for antimicrobial testing.

The antimicrobial species were produced on test coupons using the lactoperoxidase based system, containing lactoperoxidase (2 mg/L, ≥80 Units/mg), potassium iodide, (300 mg/L), glucose (12.5 g/L) and glucose oxidase (0.57 mg/L, ≥200 Units/mg), by submerging the coupon in the solution at 37° C. for 24-48 hours. Control coupons were also treated with a saline solution or a mixture of the system lacking in one of the components.

Cells were then recovered from the surface of the coupons by means of sonication, and their viability determined. Cells treated with saline only were viable ($10^5$ cells/coupon), as were those tested with the system lacking in one of the components required to produce the antimicrobial species. No viable cells were recovered from the coupons wherein cells were exposed to the antimicrobial species produced by a fully functioning LP system. This result compares favourably with similar previously reported treatment regimes using a variety of antibiotics ("Linezolid compared with eperezolid, vanocmycin, and gentamicin in an in vitro model of antimicrobial lock therapy for Staphycoccus epidermidis central venous catheter-related biofilm infections", Curtin et al., 2003, Antimicrobial Agents and Chemotherapy, Vol. 47, No. 10, p 3145-3148), wherein cells were still recoverable after 10 days with treatment of 10 g/L gentamycin and 7 days with treatment of 10 g/L vancomycin, though better results were recorded for linezolid and eperezolid. Such concentrations are far greater (up to 1,000 fold) than those that would be lethal to the same strain grown planktonically. By contrast, the concentrations of the antimicrobial species generated in the present experiment were of the same order of magnitude as those used to kill planktonic cells.

EXAMPLE 7

The susceptibility of a number of P. aeruginosa strains to the KI-Dose-150 composition was tested using the method described in Example 1. These strains were of interest as they demonstrated increased tolerance to a variety of key antibiotics typically used to treat lung infections associated with cystic fibrosis, and were recovered from the sputum of cystic fibrosis patients presenting with lung infection. The relative susceptibilities are described in Table 4. As evident from Table 4, the antibiotic tolerant strains of P. aeruginosa are no more tolerant to KI-Dose-150, indicating that the system would be effective at treating such infections when delivered to the lung. 'S' denotes sensitive, 'R' denotes resistant or increased tolerance.

TABLE 4

Susceptibility of antibiotic tolerant P. aeruginosa strains to 'KI-Dose-150'. The MIC value represents the minimum level of reactive oxygen species (hypoiodate) required to kill the strains (millimoles per litre produced over 24 hours).

| | Amikacin | Tobramycin | Ciprofloxacin | Gentamicin | MIC |
|---|---|---|---|---|---|
| PA01 (wild type) | S | S | S | S | 0.25 mM |
| R550/2012 9026 | R | R | R | R | 0.12 mM |
| R468/2012 9027 | R | S | S | S | 0.06 mM |

TABLE 4-continued

Susceptibility of antibiotic tolerant *P. aeruginosa* strains to 'KI-Dose-150'. The MIC value represents the minimum level of reactive oxygen species (hypoiodate) required to kill the strains (millimoles per litre produced over 24 hours).

| | Amikacin | Tobramycin | Ciprofloxacin | Gentamicin | MIC |
|---|---|---|---|---|---|
| R479/2012 9028 | R | R | s | R | 0.12 mM |
| R480/2012 9029 | R | s | R | R | 0.12 mM |
| *P. aeruginosa* D12 | s | s | R | s | 0.25 mM |

EXAMPLE 8

The treatment of respiratory infections by antibiotics will typically be delivered using oral or intra venous drugs. The aerosolised form of the antibiotics can also be used to counteract the poor transfer of drug from blood across the alveoli of the lung to infection sites. Various embodiments of the proposed antimicrobial composition were aerosolised using an AeroNeb nebuliser (courtesy of Aerogen Ltd.). Solutions of hydrogen peroxide/glucose/glucose oxidase/lactoerpoxidase/iodide/ or thiocyanate were passed through the nebuliser one at a time, or mixed together and passed through the nebuliser, and the aerosol collected in a sterile 25 ml container. The antimicrobial potency of the aero-solised forms was compared to un-aerosolised forms (as described in Example 1), using doubling dilutions on a multi-well plate based assay. The proposed composition did not show any decreased activity when compared to the solutions that were not aerosolised. In addition, it was demonstrated that the enzymatic system, which can be used to produce the antimicrobial species was not affected by nebulisation. Specifically, the solutions did not show any reduced enzyme activity, or decreased levels of compound present when compared to stock solutions of the same components. This model would suggest that the proposed antimicrobial system would be a good target or candidate for successful aerosol delivery to the lung to treat respiratory infections.

EXAMPLE 9

Lactoferrin is a mammalian protein that has been characterised to exercise antimicrobial properties, particularly on biofilm. As such, it is a good potential compound that could target and disrupt biofilm production in an infection model, and one that could act synergistically with a system such as the antimicrobial composition of the invention. The relative antimicrobial potencies of KI-Dose-150 and Thio-Dose-150 were tested as described in Example 1, both in the presence and absence of varying concentrations of lactoferrin. The presence of supplemented lactoferrin to the thiocyante model did not enhance the antimicrobial properties already present (ratios of lactoferrin to thiocyanate were 1:1, 1:2, 1:4). This would suggest that the presence of lactoferrin at significant concentrations does not inhibit the actions of a lactoperoxidase—thiocyanate model to produce the antimicrobial species. Planktonic cells were used, allowing the possibility that an accentuated antimicrobial effect would be noted for treatment of an actual infection.

The same ratios for lactoferrin to iodide did, however, lead to a noted two-fold increase in antimicrobial activity of the lactoperoxidase-iodide model for production of the antimicrobial species, suggesting that it would be a suitable companion in a proposed treatment regime. In the absence of lactoferrin, a 256-fold dilution of the system was still inhibitory to *E. coli*. With the addition of lactoferrin (at the three described ratios), a dilution factor of 512 was also inhibitory to the bacterial culture. Infection sites will often be composed of biofilm, which would allow an increased activity of the lactoferrin to be noted.

EXAMPLE 10

Antibiotic therapies designed for the treatment of bovine mastitis will often induce an inflammation of the udder, leading to an increase in the somatic cell count for the animal. This is disadvantageous in that the price of the sold milk depends on a low somatic cell count. A number of drugs can typically be added to counter the inflammation arising due to the intramammary infusion of an antimicrobial therapy. Prednisone (or its active form, prednisolone) is a glucocorticoid steroid used to minimise an undesired immune response. A dosage of 10-20 mg is often administered in conjunction with antibiotic based intramammary infusions to halt an increase in the somatic cell count. An in vitro experiment using a dose of the proposed lactoperoxidase system (KI-Dose-150) in the absence and presence of either predisone or prednisolone did not result in any decrease in antimicrobial potency of the composition. This would indicate that the use of a typical dose of either drug would not interfere with the ability of the composition of the invention to eradicate bacteria in the udder (or other environment), and would help minimise increase of the somatic cell count.

EXAMPLE 11

The ability of an enzymatic system to produce the antimicrobial species on a continuous basis was determined by repeat inoculations of bacterial culture to an antibacterial component containing solution. A 10 ml volume of LB growth medium was supplemented with glucose oxidase (15 µl of 2.5 mg/ml, 200 Units/mg), beta-galactosidase (30 µl, 10 mg/ml, 48,000 Units/mg), lactoperoxidase (20 µl, 4 mg/ml, 80 Units/mg) potassium iodide (30 µl, 40 mg/ml), with a final concentration of 2% lactose. Approximately $10^8$ cfu of *E. coli* ATCC 25922 were added and the mixture was incubated overnight, at 37° C. After 24 hours, no cells were recoverable to a fresh nutrient agar plate. A further inoculum of approximately $10^8$ cfu of *E. coli* ATCC 25922 cells was then added to the volume and the mixture was again allowed to incubate overnight. Similar, subsequent inoculations (ten inoculations, at one day intervals) of the broth with the bacterium did not result in growth or the recovery of bacterial cells. This result demonstrates that the concentration of the antimicrobial reactive species was held sufficiently above bactericidal levels over a significant time period.

EXAMPLE 12

The effect of substrate choice on the potency of the composition produced by various systems was determined using variations of an inhibition growth assay, firstly, where the concentration of $H_2O_2$ (produced by the enzymatic reaction of glucose and glucose oxidase) was constant and the concentration of the chosen substrates was altered. Secondly, an assay where the concentration of substrates was maintained constant, and the $H_2O_2$ levels were varied was employed.

(i) Constant $H_2O_2$

E. coli (50 µl of an overnight culture) was added to Mueller Hinton broth containing 5 µl glucose oxidase (2.5 mg/ml) and 10 µl LP (4 mg/ml). This was aliquoted (150 µl) to rows of a 96-well plate. Equal volumes (150 µl) of either potassium iodide or potassium thiocyanate (both 40 mg/ml) were added to the initial well. The samples were doubly diluted as far as well 11, leaving well 12 as a control. The plate was incubated overnight at 37° C., and the optical density measured throughout.

Result: Thiocyanate concentrations in dilutions 1 to 9 were at a level sufficient for complete inhibition of the bacteria. Iodide concentrations in dilutions 1 to 8 were at a level sufficient for complete inhibition of the bacteria. This result would initially indicate that there was no significant difference in the potency of the reactive species produced by either substrate, and whatever differences were noted could have been as a result of the difference in molarity of the concentrations.

(II) Constant Substrate

E. coli (200 µl of an overnight culture) was added to 20 ml Mueller Hinton broth already containing 40 µl LP (4 mg/ml) and 60 µl of either potassium iodide or potassium thiocyanate (40 mg/ml). This was aliquoted (150 µl) to a 96 well plate. Samples of a $H_2O_2$ producing system (2 ml 20% glucose containing 10 µl glucose oxidase, 2.5 mg/ml) were added to the initial well, and doubly diluted, leaving well 12 as a control.

Result: Using a broth with a constant thiocyanate concentration, there was inhibition in the two highest dilutions of sample ($H_2O_2$). However, on using iodide, there was inhibition of bacterial growth up to, and including, six dilutions of sample.

This results indicates that there is a significant difference in the potency of the antimicrobial species produced using an enzymatic system, which releases lower levels of hydrogen peroxide, when the substrate level is maintained at a constant level. This would imply that there would be a distinct advantage in using iodide when lower levels of $H_2O_2$ production are typical. Differences in molarity cannot explain the apparent difference in outcome when using iodide instead of thiocyanate.

Repetition of (i) and (ii) using milk as the growth medium showed very similar results and patterns. Using an alternative source of $H_2O_2$ (direct addition in this case) did not show up the peculiar outcome difference between iodide and thiocyanate.

EXAMPLE 13

A protocol was drawn up that allows an operator to determine the appropriate concentrations of the antimicrobial species of the invention for use in the inhibition/killing of bacterial cells in broth. The protocol is based on doubling dilutions of the components, similar to that used in 96-well plate described in Example 1. A bacterial culture ($10^7$ cfu/ml) is established and aliquoted to tubes (5 ml volumes added to 15 ml tubes would allow sufficient headspace for required oxygen, with the first tube to contain double the volume, 10 mls. The broth should contain sufficient appropriate sugar if using enzymes to produce $H_2O_2$, for example, glucose if using glucose oxidase, with 1-2% being typically sufficient).

An aliquot (preferably no more than 5% of the total volume of the solution, 500 µl) of the hydrogen peroxide producing components are added to the initial volume, and doubly diluted. After 24 hours the level of innate tolerance for a bacterial strain to hydrogen peroxide can be determined by the pattern of growth/no growth in the tubes. The hydrogen peroxide producing components could consist of a monosaccharide or disaccharide sugar and their appropriate cleaving enzymes (notably lactose and beta-galactosidase and glucose oxidase, or glucose and glucose oxidase) or more simply hydrogen peroxide can be added directly, or as hydrogen peroxide releasing percarbonate or citric acid, etc.

In conjunction with the test to determine the innate hydrogen peroxide sensitivity of the test strain, the same test would also be used using a reactive oxygen species producing solution (such as Thio-Dose-150 or KI-Dose-150, as described in example 1), wherein the hydrogen peroxide producing components are present, as well as the peroxidise enzyme (chloroperoxidase or lactoperoxidase, and their appropriate substrates) are also present.

Although various ratios and concentration variations of the LP system, for example, can be employed to yield antimicrobial and bactericidal concentration of the reactive species, the authors recommend a possible ratio of 75:2 of substrate to lactoperoxidase (for example, 150 mg KI and 4 mg lactoerpoxidase (at least 80 Units/mg). Similarly, if $H_2O_2$ is to be produced by the enzymatic cleavage of glucose, for example, the authors recommend a 75:2:1 of substrate, lactoperoxidase, and glucose oxidase (200 Units/mg glucose oxidase). The samples should be incubated at the appropriate temperature, and shaken overnight. Control cultures (without, for example, LP components or $H_2O_2$) should yield bacterial growth. At sufficiently high concentrations of $H_2O_2$ (initial few tubes), growth should not be observed but as the $H_2O_2$ level drops (more dilute cultures), growth will be evident. This will allow the operator to determine the innate tolerance of the strain to the actions of $H_2O_2$. Often, Streptococci strains are very susceptible to the actions of $H_2O_2$, as they lack catalase required to cleave the $H_2O_2$ molecule, whilst other species will be tolerant of $H_2O_2$ at levels of ~2 mM (some yeasts, for example). The addition of the substrate and lactoperoxidase to the initial tube should result in no growth at levels of $H_2O_2$ that were not previously inhibitory as the more potent reactive species are produced. Similarly, there will be a level at which the dilution was such that growth occurred. The difference in outcome between '$H_2O_2$ only' and '$H_2O_2$ and substrate and LP' will inform the operator as to concentration of the LP-system components necessary to kill the test strain, or to inhibit its growth over 24 or 48 hours, as required. The authors recommend choosing a concentration at which the $H_2O_2$ is not inhibitory in itself. Data described in Example 3 describes the use of an enzymatic cleavage of sugar, which allows a 'window' where the $H_2O_2$ levels produced in the solution are insufficient to cause inhibition, though sufficient to drive the production of the antimicrobial reactive oxygen species by the LP reaction (in instances where the strain does not produce catalase, and is therefore extremely susceptible to the actions of $H_2O_2$, the authors recommend using levels sufficient to kill typical catalase producing strains). A subculture to appropriate agar plate at 24/48/72 hour time points will allow the operator to determine at which concentrations the components are produced at bactericidal concentrations, as opposed to bacteriostatic levels. The composition will be determined as bacteriocidal when no more than 0.001% of the starting cell numbers are recoverable from the broth.

This test allows the operator to determine the bacteriocidal concentration of the dose, and also the concentrations of hydrogen peroxide required to produce the components using an enzymatic system, without generating inhibitory levels of hydrogen peroxide. Such information will be valuable if contemplating introducing an enzymatic system to a sensitive environment, such as the mammalian lung.

Existing statistical models will allow the operator to then 'scale up' appropriately to determine the necessary levels required to treat infections or large volumes of liquid etc, for example, the udder or lung.

EXAMPLE 14

The lower limits of each of the components in an enzymatic system, required to produce inhibitory biocidal concentrations of the antimicrobial agents, were determined (for example Table 1 and Table 5). To establish these lower limits for each component, minimum inhibitory concentrations for each were calculated using doubling dilutions on a 96-well plate, in a manner similar to that described in Example 1, wherein the concentration of the component of choice is lowered until no effect on growth is noted. In 10 ml LB broth growth medium (with 2% glucose), replete with 120 mg/L KI, 320 units LP, at least 0.5 unit glucose oxidase/ml is required to produce hydrogen peroxide. Concentrations below this resulted in insufficient hydrogen peroxide being produced to provide for the further production of the reactive oxygen species at a bactericidal concentration. Similarly, the reduction of glucose levels requires an increase of glucose oxidase levels to compensate; 1% glucose required 1 units/ml, while 0.5% glucose required 2 units/ml activity glucose oxidase. In solutions where the glucose levels and glucose oxidase levels are sufficient, the level of required iodide (or thiocyanate) substrate was approximately 0.5 mM. At levels below this, there was insufficient reactive oxygen species produced to result in effective bactericidal activity. The level of LP required for a reaction to produce the reactive oxygen species at the required concentrations was determined at 0.15 unit activity/ml (1 mM KI present). Levels below this resulted in little antibacterial activity. This embodiment of the invention suitable for the therapeutic treatment of mastitis also included beta-galactosidase to convert the lactose present in milk to glucose. An in vitro examination of the required level of this enzyme was performed in milk (5% lactose), with 1 mM KI, 0.75 units/ml glucose oxidase activity/ml (levels below this will produce a 'bottleneck' in the enzymatic pathway resulting in insufficient reactive oxygen species being produced), and 1 unit lactoperoxidase activity/ml present The required activity of beta-galactosidase lay at approximately 1.5 units activity/ml. Beta-galactosidase activity at levels below this did not result in the inhibition of bacterial growth or in killing of bacterial cells, but rather in bacterial proliferation.

EXAMPLE 15

It is possible to produce the antimicrobial reactive oxygen species of the composition of the invention before adding it to the site of infections. This may be achieved by the mixing of the required enzymatic components ensuring that the resulting reactive oxygen species (ROS; hypothiocyanate, hypoiodate, or hypochlorate) is produced outside of the treatment site. Further to this, any excess hydrogen peroxide left after the reaction can be removed by the addition of catalase (which reacts with hydrogen peroxide, producing oxygen gas and water). This may prove a very safe method of delivering the chosen ROS without the potentially disadvantageous hydrogen peroxide molecules.

Similarly, it is possible to introduce the catalase at the infection site also to help 'quench' the potential build-up of harmful hydrogen peroxide.

To demonstrate this, the potency of the KI-Dose-150 and Thio-Dose-150 compositions were tested, using the protocol described in Example 1, in a broth growth medium containing catalase (20 µl of a 4 mg/ml, >1,000 units/mg to 20 ml broth). The potency of the doses was not reversed. A 1:1024 dilution of the doses was inhibitory in the absence of catalase, and a 1:512 dilution of the doses was inhibitory in the presence of catalase.

As a comparison, the test was performed using only hydrogen peroxide (0.85 M), both in the presence and absence of catalase. The catalase level was sufficient to completely reverse the inhibitory nature of hydrogen peroxide, indicating that the catalase levels used for the experiment were sufficient to 'quench' the activity, and thus, would be appropriate component to 'mop up' excess hydrogen peroxide produced if the iodide or thiocyanate substrate is used up, but not inhibit the reaction per se when substrate is still present.

This may serve to protect mammalian tissue.

EXAMPLE 16

A further example of a pre-activated system was employed as follows: solutions (4 ml volumes) containing 0.85 M $H_2O_2$ plus none or 2.5 M NaCl/5 µl chloroperoxidase (~10,000 Units/ml) were allowed incubate. The solutions were then split and either catalase treated (50 µl of a 4 mg/ml, >1,000 units/mg) or were not catalase treated. The relative antimicrobial properties of the solutions were then tested using the protocol as described in Example 1 using *E. coli* supplemented broth. Inhibition of the bacteria was noted at >1:640 dilutions for hydrogen peroxide only, hydrogen peroxide+chloroperoxidase/NaCl, and the catalase treated hydrogen peroxide+chloroperoxidase/NaCl samples. However, there was no inhibition noted for the catalase treated hydrogen peroxide sample. This result would suggest that it is possible to remove any excess hydrogen peroxide by means of catalase treatment, without reducing the potency of the reactive oxygen species. The solutions were allowed to incubate for longer, after which time (72 hours) the result was repeated. This would suggest that this form of the ROS was relatively stable and could be prepared in advance of use.

EXAMPLE 17

The protocol described in Example 1 was used to test 'KI-Dose-150', a version lacking iodide and lactoperoxidase, as well as version lacking glucose oxidase. All three were tested against *Candida glabrata, Candida krusei, Candida tropicalis, Candida albicans* and *Saccharomyces cerevesiae*. Protocols were carried out for the *Candida* strains and *Saccharomyces* strain in nutrient broth and LB broth respectively, each supplemented with 2% glucose using the method described in Example 1. Results are presented in Table 5. It is clear from Table 5 that all strains are inhibited by the actions of 'KI-Dose-150' and that the reactive oxygen species are thus antimicrobial and not just antibacterial. The levels of hydrogen peroxide produced in these dilutions of the composition were themselves non-inhibitory to the tested strains.

TABLE 5

Susceptibility of fungal and yeast strains to 'KI-Dose-150'. The MIC value represents the minimum level of reactive oxygen species (hypoiodate) required to kill the strains (millimoles per litre produced over 24 hours)

| | MIC |
|---|---|
| Candida albicans | 0.25-0.5 mM |
| Candida tropicalis | 0.12-0.25 mM |
| Candida glabrata | 0.25-0.5 mM |
| Candida krusei | 0.25-0.5 mM |
| Saccharomyces cerevisiae | 0.12-0.25 mM |

EXAMPLE 18

The results presented in Example 3 demonstrate that there are three crucial levels of $H_2O_2$. These levels can be described using a schematic model, as illustrated in FIG. 7.

Firstly, there is a higher threshold level of $H_2O_2$, at or above which inhibition of bacterial growth occurs as a direct result of the concentration of $H_2O_2$ in the growth medium. This is not the preferable mechanism of action for an antimicrobial composition, as $H_2O_2$ is toxic to host cells, and has been linked to mammalian tissue damage, for example.

The second threshold level of $H_2O_2$ is that required for the effective production of the antimicrobial reactive oxygen species. The experiments presented herein (Example 3) describe the distinct advantage that is conferred by the use of an enzymatic method of $H_2O_2$ production, wherein the levels of $H_2O_2$ can be maintained within this required 'window' (FIG. 7) for a longer period of time (i.e. these are concentrations of $H_2O_2$ that are effective at allowing the production of the required concentration of reactive oxygen species, but that are not toxic in themselves).

Lastly, the third threshold level of $H_2O_2$ is one at which there is insufficient $H_2O_2$ to inhibit or provide for the production of the reactive oxygen species using an enzymatic system.

Using a more direct source of peroxide (such as the sodium percarbonate or hydrogen peroxide itself) results in a high initial concentration of $H_2O_2$ that quickly decreases to a level that is ineffective for the production of the desired reactive oxygen species (FIG. 7).

EXAMPLE 19

The conversion of substrate to the antimicrobial reactive oxygen species (ROS) was estimated by direct measurement of the relevant substrate concentration during conversion and, for example, after 24 hours. The various antimicrobial reactive oxygen species are relatively short-lived, but have variable half-lives depending on the substrate used, so a direct titration was not useful. For example, Thiocyanate concentrations, at 1× (1.36 mM) and 5× (6.8 mM) levels, were compared before and after incubation in a solution containing glucose, lactoperoxidase, and glucose oxidase. These were compared to a standard concentration curve of thiocyanate levels (0, 0.0625, 0.125, 0.25, 0.5, 1, 2, and 5× concentrations) using a colourometric assay as follows:

Five grams ferric chloride was suspended in 50 ml water. Any undissolved ferric chloride was removed by centrifugation, leaving ~30 ml ferric chloride solution. To cuvettes, 150 µl of the ferric solution was added, followed by the addition of 700 µl water. A volume of 10× thiocyanate was added to each cuvette (200 µl, 160 µl, 100 µl, 40 µl, 20 µl, 10 µl, 5 µl, 25 µl (1:10), 12.5 µl (1:10), 0 µl). The final volume in the cuvette was brought to 1,050 µl by the addition of water. For the sample, 50 µl of the previously incubated 1× or 5× dilutions were added, plus 150 µl water. The optical density was recorded at 460 nm, and the concentrations were then calculated using a standard curve. The resulting standard curve had an r2 value of >0.99, (see FIG. 8) indicating that it was an accurate method of determining an unknown concentration of thiocyanate.

The 1× dose (left incubating overnight with the enzyme system), read as 0.17× dose after 24 hours. Similarly, the 5× dose (left incubating overnight with the enzyme system), read as a 1.1× dose after 24 hours. Both of these results would indicate that, under these conditions, there was an 80-85% drop in thiocyanate levels. Assuming a 1:1 ratio of thiocyante loss to ROS production (in this case, OSCN−), this allows the determination of the ROS levels produced to be in the region of 1 mM, and 5 mM over the 24 hours for the 1× and 5× doses, respectively. This value can be adapted using a higher substrate concentration, whilst maintaining efficiency in conversion, at least within the range tested here.

The specific levels of ROS disclosed here as providing bactericidal and fungicidal activity are greater than the levels produced using the LP system elsewhere. The concentration dependent microcidal effect described in this application; and the ability to determine minimum inhibitory concentrations for the ROS against target strains and in various media and settings, allows the use of the composition of the invention as a targeted bacteriocidal and microcidal therapeutic and antimicrobial composition, as opposed to applications with merely general non-specific bacteriostatic effects.

EXAMPLE 20

The ability to achieve potentially therapeutic doses of the reactive oxygen species in vivo was investigated, again using a milk model. The intramammary infusion method was used to introduce the described protoype of Example 4, [150 mg KI, 4 mg lactoperoxidase (320 units), 2 mg glucose oxidase (400 units), and Beta-galactosidase, (1,350 Units)] to a bovine udder. This was performed after milking of the animal. At the next milking, a sample of milk was obtained. Aliquots (10 ml volumes) of the milk were spiked with approximately $10^7$ cfu/ml of bacterial strains (E. coli, P. aeruginosa, or S. dysgalactiae) and allowed incubate overnight at 37° C. whilst shaking. A total viable count was performed using agar plates. The milk was completely inhibitory to the strains. This would indicate the presence of the reactive oxygen species in the milk at a concentration sufficient to kill these mastitis causing organisms. This is important in demonstrating the technology as a therapeutic, Further to this, because the reactive oxygen species are relatively short-lived, it is likely that the concentration would have been higher in the udder itself, increasing the effectiveness of the treatment further.

Compositions Suitable for Administration.

A solution containing 1-100,000 Units activity glucose oxidase, 1-100,000 Units activity of lactoperoxidase, and 0.1-10,000 mg thiocyanate/iodide, and 0.01-100,000 Units activity of beta-galactosidase would be suitable to be administered to the udder of an animal as an intramammary infusion A solution containing 1-100,000 Units activity galactose oxidase, 1-100,000 Units activity of lactoperoxidase, and 0.1-10,000 mg thiocyanate/iodide, and 0.01-100,000 Units activity of beta-galactosidase would be suitable to be administered to the udder of an animal as an intramammary infusion A solution containing 1-100,000 Units activity glucose oxidase, 1-100,000 Units activity of lactoperoxidase, and 0.1-10,000 mg thiocyanate/iodide, and 0.01-100,000 mg glucose would be suitable to be administered to the udder of an animal as an intramammary infusion A solution containing 1-100,000 Units activity glucose oxidase, 1-100,000 Units activity of lactoperoxidase, and 0.1-10,000 mg thiocyanate/iodide, and 0.01-100,000 mg glucose would be suitable to be administered to the lungs for the treatment of bacterial infection as a nebulised spray.

The same solution as above containing supplemented lactoferrin (0.01-100,000 mg), prednisone (0.01-100,000 mg), or prednisolone (0.01-100,000 mg), catalase (1-1,000,000 Units) or a combination of two or more of these.

A solution containing 1-100,000 Units activity glucose oxidase, 1-100,000 Units activity of chloroperoxidase, and 0.1-10,000 mg chloride ion, and 0.01-100,000 mg glucose to be administered to the lungs for the treatment of bacterial infection as a nebulised spray.

The same solution as above containing supplemented lactoferrin (0.01-100,000 mg), prednisone (0.01-100,000 mg), or prednisolone (0.01-100,000 mg), or a combination of two or more of these. A solution containing 1-100,000 Units activity of lactoperoxidase, and 0.1-10,000 mg thiocyanate/iodide, and 0.01-100 ml hydrogen peroxide would be suitable to be administered to the lungs for the treatment of bacterial infection as a nebulised spray.

A poultice impregnated with 1-100,000 Units activity glucose oxidase, 1-100,000 Units activity of lactoperoxidase and an accompanying gel containing 0.1-10,000 mg thiocyanate/iodide, and 0.01-100,000 mg glucose to be applied to the poultice prior to its use in treating burns or open wounds of a patient.

A poultice impregnated with 1-100,000 Units activity glucose oxidase, 1-100,000 Units activity of chloroperoxidase and an accompanying gel containing 0.1-10,000 mg chloride ion, and 0.01-100,000 mg glucose to be applied to the poultice prior to its use in treating burns or open wounds of a patient.

The same poultices as above containing supplemented lactoferrin (0.01-100,000 mg), prednisone (0.01-100,000 mg), or prednisolone (0.01-100,000 mg), catalase (1-1,000,000 Units) or a combination of two or more of these. A variety of medical devices may be coated/impregnated with 1-100,000 Units activity glucose oxidase, 1-100,000 Units activity of lactoperoxidase before insertion into the body of a patient.

A pre-prepared composition containing iodide/thiocyanate ions (0.1-10,000 mg) allowed to react fully with hydrogen peroxide (0.01-100 ml) in the presence of lactoperoxidase (0.01-1,000,000 Units). The composition is catalase treated (0.01-1,000,000 Units) to remove excess hydrogen peroxide, before the composition is used to treat infection sites.

A pre-prepared composition containing chloride ions (0.1-10,000 mg) allowed to react fully with hydrogen peroxide (0.01-100 ml) in the presence of chloroperoxidase (0.01-1,000,000 Units). The composition is catalase treated (0.01-1,000,000 Units) to remove excess hydrogen peroxide, before the composition is used to treat infection sites.

A pre-prepared composition containing chloride ions (0.1-10,000 mg) allowed to react fully with sodium percarbonate (0.01-100,000 mg) in the presence of chloroperoxidase (0.01-1,000,000 Units). The composition is catalase treated (0.01-1,000,000 Units) to remove excess hydrogen peroxide, before the composition is used to treat infection sites.

A pre-prepared composition containing thiocyanate/iodide ions (0.1-10,000 mg) allowed to react fully with sodium percarbonate (0.01-100,000 mg) in the presence of lactoperoxidase (0.01-1,000,000 Units). The composition is catalase treated (0.01-1,000,000 Units) to remove excess hydrogen peroxide, before the composition is used to treat infection sites.

A pre-prepared composition containing chloride ions (0.1-10,000 mg) allowed to react fully with glucose (0.01-100,000 mg) and glucose oxidase (0.1-1,000,000 Units) in the presence of chloroperoxidase (0.01-1,000,000 Units). The composition is catalase treated (0.01-1,000,000 Units) to remove excess hydrogen peroxide, before the composition is used to treat infection sites.

A pre-prepared composition containing thiocyanate/iodide ions (0.1-10,000 mg) allowed to react fully with glucose (0.01-100,000 mg) and glucose oxidase (0.1-1,000,000 Units) in the presence of lactoperoxidase (0.01-1,000,000 Units). The composition is catalase treated (0.01-1,000,000 Units) to remove excess hydrogen peroxide, before the composition is used to treat infection sites.

The above pre-prepared solutions supplemented with lactoferrin (0.001 mg-10,000 mg), prednisone (0.001 mg-10,000 mg), or prednisolone (0.001 mg-10,000 mg), either individually or a combination of two or more.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A composition for treating bovine mastitis, the composition consisting of components for producing a reactive oxygen species, wherein the reactive oxygen species is hypoiodite ($IO^-$), wherein the components for producing a reactive oxygen species are (i) lactoperoxidase, (ii) an oxidizable substrate, wherein the oxidizable substrate is potassium iodide or sodium iodide, and (iii) hydrogen peroxide, or a source of hydrogen peroxide;

wherein the composition is free of glucose and galactose, wherein the composition is microbiocidal, wherein the composition is optionally in the form of a solution, wherein the composition is capable of releasing the reactive oxygen species to an infection site for at least 24hours, and wherein the composition is capable of delivering to the infection site the reactive oxygen species to a level of at least 0.4 millimoles per litre of liquid present at the infection site, over a 24-hour period.

2. The composition as claimed in claim 1 capable of delivering the reactive oxygen species to a level of at least 0.5 millimoles per litre, over a 24 hour period.

3. The composition as claimed in claim 1 where the source of hydrogen peroxide is a solution of the hydrogen peroxide.

4. The composition as claimed in claim 1 where the hydrogen peroxide is released by a hydrogen peroxide releasing compound selected from the group comprising percarbonates, citric acid and perhydrates, or by enzymatic methods.

5. The composition as claimed in claim 1 where the source of hydrogen peroxide is an enzymatic reaction between a sugar and its appropriate oxidoreductase.

6. The composition as claimed in claim 5 wherein the oxidoreductase is galactose oxidase and/or glucose oxidase.

7. The composition as claimed in claim 6 wherein the source of hydrogen peroxide further comprises free monosaccharide sugar(s).

8. The composition as claimed in claim 5 wherein the source of hydrogen peroxide further comprises a disaccharide sugar, and its corresponding glycoside hydrolase to produce a source of hydrogen peroxide.

9. The composition as claimed in claim 8 wherein the glycoside hydrolase is Beta-galactosidase, and the disaccharide sugar is lactose.

10. The composition as claimed in claim 1 wherein a glycoside hydrolase and/or an oxidoreductase is used to react with sugars present at the infection site as a source of hydrogen peroxide.

11. The composition as claimed in claim 5 wherein an additional source of hydrogen peroxide is derived from the reaction of a polyol with its relative oxidase enzyme.

12. The composition as claimed in claim 11 wherein the polyol is glycerol and its relative oxidase enzyme is glycerol oxidase, or wherein the polyol is mannitol and its relative oxidase enzyme is mannitol oxidase.

13. The composition as claimed in claim 1 wherein the hydrogen peroxide is produced from the enzymatic reaction of L-amino acids with L-amino acid oxidase or xanthine and xanthine oxidase.

14. An intramammary infusion delivery device loaded with the composition as claimed in claim 1.

15. The composition as claimed in claim 1 where the composition is prepared as an emulsion, a solution or dried product.

16. The composition as claimed in claim 1 wherein the composition is adhered to the surface of a medical device.

17. The composition as claimed in claim 1 where the components are allowed to react before addition to the infection site.

18. The composition as claimed in claim 1 where the components are allowed to react before addition to the infection site, and treated with catalase to remove excess hydrogen peroxide.

19. The composition as claimed in claim 1, where the composition is capable of releasing the reactive oxygen species to an infection site for up to 10 days.

20. The composition as claimed in claim 1, wherein the composition is free of sodium percarbonate.

\* \* \* \* \*